(12) United States Patent
Frohman et al.

(10) Patent No.: US 6,379,665 B1
(45) Date of Patent: Apr. 30, 2002

(54) PHOSPHOLIPASE D POLYPEPTIDE AND DNA SEQUENCES

(75) Inventors: Michael A. Frohman, Setauket; Andrew J. Morris, Mt. Sinai; Joanne Engebrecht, Stony Brook, all of NY (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/536,224

(22) Filed: Mar. 27, 2000

Related U.S. Application Data

(62) Division of application No. 08/968,752, filed on Aug. 13, 1997, now Pat. No. 6,043,073.
(60) Provisional application No. 60/025,469, filed on Sep. 5, 1996.
(51) Int. Cl.[7] ............... A61K 38/46; C12N 9/20; C12N 1/20; C12N 15/00; C07H 21/04
(52) U.S. Cl. ............ 424/94.6; 435/198; 435/252.3; 435/320.1; 536/23.2; 536/23.5; 536/23.6; 530/350
(58) Field of Search ............ 424/94.6; 435/198, 435/252.3, 320.1; 536/23.2, 23.5, 23.6; 530/350

(56) References Cited

PUBLICATIONS

Hammond et al. J. Biol. Chem. 270(50): 29640–43, Dec. 15, 1995.*

* cited by examiner

*Primary Examiner*—Tekchand Saidha
(74) *Attorney, Agent, or Firm*—Greg Giotta

(57) ABSTRACT

Provided are novel phospholipase D DNA and amino acid sequences. The sequences are useful in methods and compositions for identifying phospholipase D mediator molecules which are in turn useful in therapeutic pharmaceutical compositions for treating rheumatoid arthritis, psoriasis, ulcerative colitis, in wound healing and for treating other diseases or conditions characterized by exhibition of an inflammatory response or in the treatment of cancer and other diseases characterized by pathogenic mitogenicity.

11 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3222 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..3222

(xi) SEQUENCE DESCRIPTION: SEQ ID NO:1:

```
ATG TCA CTG AAA AAC GAG CCA CGG GTA AAT A CC TCT GCA CTG CAG AAA      48
Met Ser Leu Lys Asn Glu Pro Arg Val Asn T hr Ser Ala Leu Gln Lys
 1               5                  10                  15
```

```
ATT GCT GCT GAC ATG AGT AAT ATC ATA GAA A AT CTG GAC ACG CGG GAA         96
Ile Ala Ala Asp Met Ser Asn Ile Ile Glu A sn Leu Asp Thr Arg Glu
             20                  25                  30

CTC CAC TTT GAG GGA GAG GAG GTA GAC TAC G AC GTG TCT CCC AGC GAT        144
Leu His Phe Glu Gly Glu Glu Val Asp Tyr A sp Val Ser Pro Ser Asp
         35                  40                  45

CCC AAG ATA CAA GAA GTG TAT ATC CCT TTC T CT GCT ATT TAT AAC ACT        192
Pro Lys Ile Gln Glu Val Tyr Ile Pro Phe S er Ala Ile Tyr Asn Thr
     50                  55                  60

CAA GGA TTT AAG GAG CCT AAT ATA CAG ACG T AT CTC TCC GGC TGT CCA        240
Gln Gly Phe Lys Glu Pro Asn Ile Gln Thr T yr Leu Ser Gly Cys Pro
 65                  70                  75                  80

ATA AAA GCA CAA GTT CTG GAA GTG GAA CGC T TC ACA TCT ACA ACA AGG        288
Ile Lys Ala Gln Val Leu Glu Val Glu Arg P he Thr Ser Thr Thr Arg
                 85                  90                  95

GTA CCA AGT ATT AAT CTT TAC ACT ATT GAA T TA ACA CAT GGG GAA TTT        336
Val Pro Ser Ile Asn Leu Tyr Thr Ile Glu L eu Thr His Gly Glu Phe
             100                 105                 110

AAA TGG CAA GTT AAG AGG AAA TTC AAG CAT T TT CAA GAA TTT CAC AGA        384
Lys Trp Gln Val Lys Arg Lys Phe Lys His P he Gln Glu Phe His Arg
         115                 120                 125

GAG CTG CTC AAG TAC AAA GCC TTT ATC CGC A TC CCC ATT CCC ACT AGA        432
Glu Leu Leu Lys Tyr Lys Ala Phe Ile Arg I le Pro Ile Pro Thr Arg
     130                 135                 140

AGA CAC ACG TTT AGG AGG CAA AAC GTC AGA G AG GAG CCT CGA GAG ATG        480
Arg His Thr Phe Arg Arg Gln Asn Val Arg G lu Glu Pro Arg Glu Met
145                 150                 155                 160

CCC AGT TTG CCC CGT TCA TCT GAA AAC ATG A TA AGA GAA GAA CAA TTC        528
Pro Ser Leu Pro Arg Ser Ser Glu Asn Met I le Arg Glu Glu Gln Phe
                 165                 170                 175

CTT GGT AGA AGA AAA CAA CTG GAA GAT TAC T TG ACA AAG ATA CTA AAA        576
Leu Gly Arg Arg Lys Gln Leu Glu Asp Tyr L eu Thr Lys Ile Leu Lys
             180                 185                 190

ATG CCC ATG TAT AGA AAC TAT CAT GCC ACA A CA GAG TTT CTT GAT ATA        624
Met Pro Met Tyr Arg Asn Tyr His Ala Thr T hr Glu Phe Leu Asp Ile
         195                 200                 205

AGC CAG CTG TCT TTC ATC CAT GAT TTG GGA C CA AAG GGC ATA GAA GGT        672
Ser Gln Leu Ser Phe Ile His Asp Leu Gly P ro Lys Gly Ile Glu Gly
     210                 215                 220

ATG ATA ATG AAA AGA TCT GGA GGA CAC AGA A TA CCA GGC TTG AAT TGC        720
Met Ile Met Lys Arg Ser Gly Gly His Arg I le Pro Gly Leu Asn Cys
225                 230                 235                 240

TGT GGT CAG GGA AGA GCC TGC TAC AGA TGG T CA AAA AGA TGG TTA ATA        768
Cys Gly Gln Gly Arg Ala Cys Tyr Arg Trp S er Lys Arg Trp Leu Ile
                 245                 250                 255

GTG AAA GAT TCC TTT TTA TTG TAT ATG AAA C CA GAC AGC GGT GCC ATT        816
Val Lys Asp Ser Phe Leu Leu Tyr Met Lys P ro Asp Ser Gly Ala Ile
             260                 265                 270

GCC TTC GTC CTG CTG GTA GAC AAA GAA TTC A AA ATT AAG GTG GGG AAG        864
Ala Phe Val Leu Leu Val Asp Lys Glu Phe L ys Ile Lys Val Gly Lys
         275                 280                 285

AAG GAG ACA GAA ACG AAA TAT GGA ATC CGA A TT GAT AAT CTT TCA AGG        912
Lys Glu Thr Glu Thr Lys Tyr Gly Ile Arg I le Asp Asn Leu Ser Arg
     290                 295                 300

ACA CTT ATT TTA AAA TGC AAC AGC TAT AGA C AT GCT CGG TGG TGG GGA        960
Thr Leu Ile Leu Lys Cys Asn Ser Tyr Arg H is Ala Arg Trp Trp Gly
305                 310                 315                 320

GGG GCT ATA GAA GAA TTC ATC CAG AAA CAT G GC ACC AAC TTT CTC AAA       1008
Gly Ala Ile Glu Glu Phe Ile Gln Lys His G ly Thr Asn Phe Leu Lys
                 325                 330                 335
```

```
GAT CAT CGA TTT GGG TCA TAT GCT GCT ATC C AA GAG AAT GCT TTA GCT     1056
Asp His Arg Phe Gly Ser Tyr Ala Ala Ile G ln Glu Asn Ala Leu Ala
            340                 345                 350

AAA TGG TAT GTT AAT GCC AAA GGA TAT TTT G AA GAT GTG GCA AAT GCA     1104
Lys Trp Tyr Val Asn Ala Lys Gly Tyr Phe G lu Asp Val Ala Asn Ala
            355                 360                 365

ATG GAA GAG GCA AAT GAA GAG ATT TTT ATC A CA GAC TGG TGG CTG AGT     1152
Met Glu Glu Ala Asn Glu Glu Ile Phe Ile T hr Asp Trp Trp Leu Ser
            370                 375                 380

CCA GAA ATC TTC CTG AAA CGC CCA GTG GTT G AG GGA AAT CGT TGG AGG     1200
Pro Glu Ile Phe Leu Lys Arg Pro Val Val G lu Gly Asn Arg Trp Arg
385                 390                 395                 400

TTG GAC TGC ATT CTT AAA CGA AAA GCA CAA C AA GGA GTG AGG ATC TTC     1248
Leu Asp Cys Ile Leu Lys Arg Lys Ala Gln G ln Gly Val Arg Ile Phe
            405                 410                 415

ATA ATG CTC TAC AAA GAG GTG GAA CTC GCT C TT GGC ATC AAT AGT GAA     1296
Ile Met Leu Tyr Lys Glu Val Glu Leu Ala L eu Gly Ile Asn Ser Glu
            420                 425                 430

TAC ACC AAG AGG ACT TTG ATG CGT CTA CAT C CC AAC ATA AAG GTG ATG     1344
Tyr Thr Lys Arg Thr Leu Met Arg Leu His P ro Asn Ile Lys Val Met
            435                 440                 445

AGA CAC CCG GAT CAT GTG TCA TCC ACC GTC T AT TTG TGG GCT CAC CAT     1392
Arg His Pro Asp His Val Ser Ser Thr Val T yr Leu Trp Ala His His
            450                 455                 460

GAG AAG CTT GTC ATC ATT GAC CAA TCG GTG G CC TTT GTG GGA GGG ATT     1440
Glu Lys Leu Val Ile Ile Asp Gln Ser Val A la Phe Val Gly Gly Ile
465                 470                 475                 480

GAC CTG GCC TAT GGA AGG TGG GAC GAC AAT G AG CAC AGA CTC ACA GAC     1488
Asp Leu Ala Tyr Gly Arg Trp Asp Asp Asn G lu His Arg Leu Thr Asp
            485                 490                 495

GTG GGC AGT GTG AAG CGG GTC ACT TCA GGA C CG TCT CTG GGT TCC CTC     1536
Val Gly Ser Val Lys Arg Val Thr Ser Gly P ro Ser Leu Gly Ser Leu
            500                 505                 510

CCA CCT GCC GCA ATG GAG TCT ATG GAA TCC T TA AGA CTC AAA GAT AAA     1584
Pro Pro Ala Ala Met Glu Ser Met Glu Ser L eu Arg Leu Lys Asp Lys
            515                 520                 525

AAT GAG CCT GTT CAA AAC CTA CCC ATC CAG A AG AGT ATT GAT GAT GTG     1632
Asn Glu Pro Val Gln Asn Leu Pro Ile Gln L ys Ser Ile Asp Asp Val
            530                 535                 540

GAT TCA AAA CTG AAA GGA ATA GGA AAG CCA A GA AAG TTC TCC AAA TTT     1680
Asp Ser Lys Leu Lys Gly Ile Gly Lys Pro A rg Lys Phe Ser Lys Phe
545                 550                 555                 560

AGT CTC TAC AAG CAG CTC CAC AGG CAC CAC C TG CAC GAC GCA GAT AGC     1728
Ser Leu Tyr Lys Gln Leu His Arg His His L eu His Asp Ala Asp Ser
            565                 570                 575

ATC AGC AGC ATT GAC AGC ACC TCC AGT TAT T TT AAT CAC TAT AGA AGT     1776
Ile Ser Ser Ile Asp Ser Thr Ser Ser Tyr P he Asn His Tyr Arg Ser
            580                 585                 590

CAT CAC AAT TTA ATC CAT GGT TTA AAA CCC C AC TTC AAA CTC TTT CAC     1824
His His Asn Leu Ile His Gly Leu Lys Pro H is Phe Lys Leu Phe His
            595                 600                 605

CCG TCC AGT GAG TCT GAG CAA GGA CTC ACT A GA CCT CAT GCT GAT ACC     1872
Pro Ser Ser Glu Ser Glu Gln Gly Leu Thr A rg Pro His Ala Asp Thr
            610                 615                 620

GGG TCC ATC CGT AGT TTA CAG ACA GGT GTG G GA GAG CTG CAT GGG GAA     1920
Gly Ser Ile Arg Ser Leu Gln Thr Gly Val G ly Glu Leu His Gly Glu
625                 630                 635                 640

ACC AGA TTC TGG CAT GGA AAG GAC TAC TGC A AT TTC GTC TTC AAA GAC     1968
Thr Arg Phe Trp His Gly Lys Asp Tyr Cys A sn Phe Val Phe Lys Asp
```

```
                    645                650                  655
TGG GTT CAA CTT GAT AAA CCT TTT GCT GAT T TC ATT GAC AGG TAC TCC    2016
Trp Val Gln Leu Asp Lys Pro Phe Ala Asp P he Ile Asp Arg Tyr Ser
                660                665                670

ACG CCC CGG ATG CCC TGG CAT GAC ATT GCC T CT GCA GTC CAC GGG AAG    2064
Thr Pro Arg Met Pro Trp His Asp Ile Ala S er Ala Val His Gly Lys
            675                680                685

GCG GCT CGT GAT GTG GCA CGT CAC TTC ATC C AG CGC TGG AAC TTC ACA    2112
Ala Ala Arg Asp Val Ala Arg His Phe Ile G ln Arg Trp Asn Phe Thr
        690                695                700

AAA ATT ATG AAA TCA AAA TAT CGG TCC CTT T CT TAT CCT TTT CTG CTT    2160
Lys Ile Met Lys Ser Lys Tyr Arg Ser Leu S er Tyr Pro Phe Leu Leu
705                710                715                720

CCA AAG TCT CAA ACA ACA GCC CAT GAG TTG A GA TAT CAA GTG CCT GGG    2208
Pro Lys Ser Gln Thr Thr Ala His Glu Leu A rg Tyr Gln Val Pro Gly
                725                730                735

TCT GTC CAT GCT AAC GTA CAG TTG CTC CGC T CT GCT GCT GAT TGG TCT    2256
Ser Val His Ala Asn Val Gln Leu Leu Arg S er Ala Ala Asp Trp Ser
            740                745                750

GCT GGT ATA AAG TAC CAT GAA GAG TCC ATC C AC GCC GCT TAC GTC CAT    2304
Ala Gly Ile Lys Tyr His Glu Glu Ser Ile H is Ala Ala Tyr Val His
        755                760                765

GTG ATA GAG AAC AGC AGG CAC TAT ATC TAT A TC GAA AAC CAG TTT TTC    2352
Val Ile Glu Asn Ser Arg His Tyr Ile Tyr I le Glu Asn Gln Phe Phe
    770                775                780

ATA AGC TGT GCT GAT GAC AAA GTT GTG TTC A AC AAG ATA GGC GAT GCC    2400
Ile Ser Cys Ala Asp Asp Lys Val Val Phe A sn Lys Ile Gly Asp Ala
785                790                795                800

ATT GCC CAG AGG ATC CTG AAA GCT CAC AGG G AA AAC CAG AAA TAC CGG    2448
Ile Ala Gln Arg Ile Leu Lys Ala His Arg G lu Asn Gln Lys Tyr Arg
                805                810                815

GTA TAT GTC GTG ATA CCA CTT CTG CCA GGG T TC GAA GGA GAC ATT TCA    2496
Val Tyr Val Val Ile Pro Leu Leu Pro Gly P he Glu Gly Asp Ile Ser
            820                825                830

ACC GGC GGA GGA AAT GCT CTA CAG GCA ATC A TG CAC TTC AAC TAC AGA    2544
Thr Gly Gly Gly Asn Ala Leu Gln Ala Ile M et His Phe Asn Tyr Arg
        835                840                845

ACC ATG TGC AGA GGA GAA AAT TCC ATC CTT G GA CAG TTA AAA GCA GAG    2592
Thr Met Cys Arg Gly Glu Asn Ser Ile Leu G ly Gln Leu Lys Ala Glu
    850                855                860

CTT GGT AAT CAG TGG ATA AAT TAC ATA TCA T TC TGT GGT CTT AGA ACA    2640
Leu Gly Asn Gln Trp Ile Asn Tyr Ile Ser P he Cys Gly Leu Arg Thr
865                870                875                880

CAT GCA GAG CTC GAA GGA AAC CTA GTA ACT G AG CTT ATC TAT GTC CAC    2688
His Ala Glu Leu Glu Gly Asn Leu Val Thr G lu Leu Ile Tyr Val His
                885                890                895

AGC AAG TTG TTA ATT GCT GAT GAT AAC ACT G TT ATT ATT GGC TCT GCC    2736
Ser Lys Leu Leu Ile Ala Asp Asp Asn Thr V al Ile Ile Gly Ser Ala
            900                905                910

AAC ATA AAT GAC CGC AGC ATG CTG GGA AAG C GT GAC AGT GAA ATG GCT    2784
Asn Ile Asn Asp Arg Ser Met Leu Gly Lys A rg Asp Ser Glu Met Ala
        915                920                925

GTC ATT GTG CAA GAT ACA GAG ACT GTT CCT T CA GTA ATG GAT GGA AAA    2832
Val Ile Val Gln Asp Thr Glu Thr Val Pro S er Val Met Asp Gly Lys
    930                935                940

GAG TAC CAA GCT GGC CGG TTT GCC CGA GGA C TT CGG CTA CAG TGC TTT    2880
Glu Tyr Gln Ala Gly Arg Phe Ala Arg Gly L eu Arg Leu Gln Cys Phe
945                950                955                960

AGG GTT GTC CTT GGC TAT CTT GAT GAC CCA A GT GAG GAC ATT CAG GAT    2928
```

-continued

```
Arg Val Val Leu Gly Tyr Leu Asp Asp Pro S er Glu Asp Ile Gln Asp
            965                 970                 975

CCA GTG AGT GAC AAA TTC TTC AAG GAG GTG T GG GTT TCA ACA GCA GCT         2976
Pro Val Ser Asp Lys Phe Phe Lys Glu Val T rp Val Ser Thr Ala Ala
            980                 985                 990

CGA AAT GCT ACA ATT TAT GAC AAG GTT TTC C GG TGC CTT CCC AAT GAT         3024
Arg Asn Ala Thr Ile Tyr Asp Lys Val Phe A rg Cys Leu Pro Asn Asp
            995                 1000                1005

GAA GTA CAC AAT TTA ATT CAG CTG AGA GAC T TT ATA AAC AAG CCC GTA         3072
Glu Val His Asn Leu Ile Gln Leu Arg Asp P he Ile Asn Lys Pro Val
            1010                1015                1020

TTA GCT AAG GAA GAT CCC ATT CGA GCT GAG G AG GAA CTG AAG AAG ATC         3120
Leu Ala Lys Glu Asp Pro Ile Arg Ala Glu G lu Glu Leu Lys Lys Ile
1025            103 0               1035                1040

CGT GGA TTT TTG GTG CAA TTC CCC TTT TAT T TC TTG TCT GAA GAA AGC         3168
Arg Gly Phe Leu Val Gln Phe Pro Phe Tyr P he Leu Ser Glu Glu Ser
            1045                1050                1055

CTA CTG CCT TCT GTT GGG ACC AAA GAG GCC A TA GTG CCC ATG GAG GTT         3216
Leu Leu Pro Ser Val Gly Thr Lys Glu Ala I le Val Pro Met Glu Val
            1060                1065                1070

TGG ACT                                                                  3222
Trp Thr
```

(2) INFORMATION FOR SEQ ID NO:2:

(i) SEQUENCE CHARACTERISTICS:
        (A) LENGTH: 1074 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Leu Lys Asn Glu Pro Arg Val Asn T hr Ser Ala Leu Gln Lys
 1               5                  10                  15

Ile Ala Ala Asp Met Ser Asn Ile Ile Glu A sn Leu Asp Thr Arg Glu
            20                  25                  30

Leu His Phe Glu Gly Glu Glu Val Asp Tyr A sp Val Ser Pro Ser Asp
            35                  40                  45

Pro Lys Ile Gln Glu Val Tyr Ile Pro Phe S er Ala Ile Tyr Asn Thr
 50                  55                  60

Gln Gly Phe Lys Glu Pro Asn Ile Gln Thr T yr Leu Ser Gly Cys Pro
 65                  70                  75                  80

Ile Lys Ala Gln Val Leu Glu Val Glu Arg P he Thr Ser Thr Thr Arg
            85                  90                  95

Val Pro Ser Ile Asn Leu Tyr Thr Ile Glu L eu Thr His Gly Glu Phe
            100                 105                 110

Lys Trp Gln Val Lys Arg Lys Phe Lys His P he Gln Glu Phe His Arg
            115                 120                 125

Glu Leu Leu Lys Tyr Lys Ala Phe Ile Arg I le Pro Ile Pro Thr Arg
            130                 135                 140

Arg His Thr Phe Arg Arg Gln Asn Val Arg G lu Glu Pro Arg Glu Met
145                 150                 155                 160

Pro Ser Leu Pro Arg Ser Ser Glu Asn Met I le Arg Glu Glu Gln Phe
            165                 170                 175

Leu Gly Arg Arg Lys Gln Leu Glu Asp Tyr L eu Thr Lys Ile Leu Lys
            180                 185                 190

Met Pro Met Tyr Arg Asn Tyr His Ala Thr T hr Glu Phe Leu Asp Ile
```

```
              195                 200                     205
Ser Gln Leu Ser Phe Ile His Asp Leu Gly Pro Lys Gly Ile Glu Gly
    210                 215                 220
Met Ile Met Lys Arg Ser Gly His Arg Ile Pro Gly Leu Asn Cys
225                 230                 235                 240
Cys Gly Gln Gly Arg Ala Cys Tyr Arg Trp Ser Lys Arg Trp Leu Ile
                245                 250                 255
Val Lys Asp Ser Phe Leu Leu Tyr Met Lys Pro Asp Ser Gly Ala Ile
                260                 265                 270
Ala Phe Val Leu Leu Val Asp Lys Glu Phe Lys Ile Lys Val Gly Lys
            275                 280                 285
Lys Glu Thr Glu Thr Lys Tyr Gly Ile Arg Ile Asp Asn Leu Ser Arg
    290                 295                 300
Thr Leu Ile Leu Lys Cys Asn Ser Tyr Arg His Ala Arg Trp Trp Gly
305                 310                 315                 320
Gly Ala Ile Glu Glu Phe Ile Gln Lys His Gly Thr Asn Phe Leu Lys
                325                 330                 335
Asp His Arg Phe Gly Ser Tyr Ala Ala Ile Gln Glu Asn Ala Leu Ala
            340                 345                 350
Lys Trp Tyr Val Asn Ala Lys Gly Tyr Phe Glu Asp Val Ala Asn Ala
        355                 360                 365
Met Glu Glu Ala Asn Glu Glu Ile Phe Ile Thr Asp Trp Trp Leu Ser
    370                 375                 380
Pro Glu Ile Phe Leu Lys Arg Pro Val Val Glu Gly Asn Arg Trp Arg
385                 390                 395                 400
Leu Asp Cys Ile Leu Lys Arg Lys Ala Gln Gln Gly Val Arg Ile Phe
                405                 410                 415
Ile Met Leu Tyr Lys Glu Val Glu Leu Ala Leu Gly Ile Asn Ser Glu
            420                 425                 430
Tyr Thr Lys Arg Thr Leu Met Arg Leu His Pro Asn Ile Lys Val Met
        435                 440                 445
Arg His Pro Asp His Val Ser Ser Thr Val Tyr Leu Trp Ala His His
    450                 455                 460
Glu Lys Leu Val Ile Ile Asp Gln Ser Val Ala Phe Val Gly Gly Ile
465                 470                 475                 480
Asp Leu Ala Tyr Gly Arg Trp Asp Asp Asn Glu His Arg Leu Thr Asp
                485                 490                 495
Val Gly Ser Val Lys Arg Val Thr Ser Gly Pro Ser Leu Gly Ser Leu
            500                 505                 510
Pro Pro Ala Ala Met Glu Ser Met Glu Ser Leu Arg Leu Lys Asp Lys
        515                 520                 525
Asn Glu Pro Val Gln Asn Leu Pro Ile Gln Lys Ser Ile Asp Asp Val
    530                 535                 540
Asp Ser Lys Leu Lys Gly Ile Gly Lys Pro Arg Lys Phe Ser Lys Phe
545                 550                 555                 560
Ser Leu Tyr Lys Gln Leu His Arg His Leu His Asp Ala Asp Ser
                565                 570                 575
Ile Ser Ser Ile Asp Ser Thr Ser Ser Tyr Phe Asn His Tyr Arg Ser
            580                 585                 590
His His Asn Leu Ile His Gly Leu Lys Pro His Phe Lys Leu Phe His
        595                 600                 605
Pro Ser Ser Glu Ser Glu Gln Gly Leu Thr Arg Pro His Ala Asp Thr
    610                 615                 620
```

```
Gly Ser Ile Arg Ser Leu Gln Thr Gly Val Gly Glu Leu His Gly Glu
625                 630                 635                 640

Thr Arg Phe Trp His Gly Lys Asp Tyr Cys Asn Phe Val Phe Lys Asp
            645                 650                 655

Trp Val Gln Leu Asp Lys Pro Phe Ala Asp Phe Ile Asp Arg Tyr Ser
                660                 665                 670

Thr Pro Arg Met Pro Trp His Asp Ile Ala Ser Ala Val His Gly Lys
            675                 680                 685

Ala Ala Arg Asp Val Ala Arg His Phe Ile Gln Arg Trp Asn Phe Thr
690                 695                 700

Lys Ile Met Lys Ser Lys Tyr Arg Ser Leu Ser Tyr Pro Phe Leu Leu
705                 710                 715                 720

Pro Lys Ser Gln Thr Thr Ala His Glu Leu Arg Tyr Gln Val Pro Gly
                725                 730                 735

Ser Val His Ala Asn Val Gln Leu Leu Arg Ser Ala Ala Asp Trp Ser
            740                 745                 750

Ala Gly Ile Lys Tyr His Glu Glu Ser Ile His Ala Ala Tyr Val His
            755                 760                 765

Val Ile Glu Asn Ser Arg His Tyr Ile Tyr Ile Glu Asn Gln Phe Phe
770                 775                 780

Ile Ser Cys Ala Asp Asp Lys Val Val Phe Asn Lys Ile Gly Asp Ala
785                 790                 795                 800

Ile Ala Gln Arg Ile Leu Lys Ala His Arg Glu Asn Gln Lys Tyr Arg
                805                 810                 815

Val Tyr Val Val Ile Pro Leu Leu Pro Gly Phe Glu Gly Asp Ile Ser
                820                 825                 830

Thr Gly Gly Gly Asn Ala Leu Gln Ala Ile Met His Phe Asn Tyr Arg
            835                 840                 845

Thr Met Cys Arg Gly Glu Asn Ser Ile Leu Gly Gln Leu Lys Ala Glu
            850                 855                 860

Leu Gly Asn Gln Trp Ile Asn Tyr Ile Ser Phe Cys Gly Leu Arg Thr
865                 870                 875                 880

His Ala Glu Leu Glu Gly Asn Leu Val Thr Glu Leu Ile Tyr Val His
                885                 890                 895

Ser Lys Leu Leu Ile Ala Asp Asp Asn Thr Val Ile Ile Gly Ser Ala
                900                 905                 910

Asn Ile Asn Asp Arg Ser Met Leu Gly Lys Arg Asp Ser Glu Met Ala
            915                 920                 925

Val Ile Val Gln Asp Thr Glu Thr Val Pro Ser Val Met Asp Gly Lys
            930                 935                 940

Glu Tyr Gln Ala Gly Arg Phe Ala Arg Gly Leu Arg Leu Gln Cys Phe
945                 950                 955                 960

Arg Val Val Leu Gly Tyr Leu Asp Asp Pro Ser Glu Asp Ile Gln Asp
                965                 970                 975

Pro Val Ser Asp Lys Phe Phe Lys Glu Val Trp Val Ser Thr Ala Ala
            980                 985                 990

Arg Asn Ala Thr Ile Tyr Asp Lys Val Phe Arg Cys Leu Pro Asn Asp
            995                 1000                1005

Glu Val His Asn Leu Ile Gln Leu Arg Asp Phe Ile Asn Lys Pro Val
            1010                1015                1020

Leu Ala Lys Glu Asp Pro Ile Arg Ala Glu Glu Leu Lys Lys Ile
1025                1030                1035                1040
```

Arg Gly Phe Leu Val Gln Phe Pro Phe Tyr Phe Leu Ser Glu Glu Ser
                1045                1050                1055

Leu Leu Pro Ser Val Gly Thr Lys Glu Ala Ile Val Pro Met Glu Val
            1060                1065                1070

Trp Thr (2) INFORMATION FOR SEQ ID NO:3:

(i) SEQUENCE CHARACTERISTICS:
        (A) LENGTH: 3108 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..3108

(xi) SEQUENCE DESCRIPTION: SEQ ID NO:3:

| | | |
|---|---|---|
| ATG TCA CTG AAA AAC GAG CCA CGG GTA AAT ACC TCT GCA CTG CAG AAA<br>Met Ser Leu Lys Asn Glu Pro Arg Val Asn Thr Ser Ala Leu Gln Lys<br>1               5                   10                  15 | 48 | |
| ATT GCT GCT GAC ATG AGT AAT ATC ATA GAA AAT CTG GAC ACG CGG GAA<br>Ile Ala Ala Asp Met Ser Asn Ile Ile Glu Asn Leu Asp Thr Arg Glu<br>            20                  25                  30 | 96 | |
| CTC CAC TTT GAG GGA GAG GAG GTA GAC TAC GAC GTG TCT CCC AGC GAT<br>Leu His Phe Glu Gly Glu Glu Val Asp Tyr Asp Val Ser Pro Ser Asp<br>        35                  40                  45 | 144 | |
| CCC AAG ATA CAA GAA GTG TAT ATC CCT TTC TCT GCT ATT TAT AAC ACT<br>Pro Lys Ile Gln Glu Val Tyr Ile Pro Phe Ser Ala Ile Tyr Asn Thr<br>    50                  55                  60 | 192 | |
| CAA GGA TTT AAG GAG CCT AAT ATA CAG ACG TAT CTC TCC GGC TGT CCA<br>Gln Gly Phe Lys Glu Pro Asn Ile Gln Thr Tyr Leu Ser Gly Cys Pro<br>65                  70                  75                  80 | 240 | |
| ATA AAA GCA CAA GTT CTG GAA GTG GAA CGC TTC ACA TCT ACA ACA AGG<br>Ile Lys Ala Gln Val Leu Glu Val Glu Arg Phe Thr Ser Thr Thr Arg<br>                85                  90                  95 | 288 | |
| GTA CCA AGT ATT AAT CTT TAC ACT ATT GAA TTA ACA CAT GGG GAA TTT<br>Val Pro Ser Ile Asn Leu Tyr Thr Ile Glu Leu Thr His Gly Glu Phe<br>            100                 105                 110 | 336 | |
| AAA TGG CAA GTT AAG AGG AAA TTC AAG CAT TTT CAA GAA TTT CAC AGA<br>Lys Trp Gln Val Lys Arg Lys Phe Lys His Phe Gln Glu Phe His Arg<br>        115                 120                 125 | 384 | |
| GAG CTG CTC AAG TAC AAA GCC TTT ATC CGC ATC CCC ATT CCC ACT AGA<br>Glu Leu Leu Lys Tyr Lys Ala Phe Ile Arg Ile Pro Ile Pro Thr Arg<br>    130                 135                 140 | 432 | |
| AGA CAC ACG TTT AGG AGG CAA AAC GTC AGA GAG GAG CCT CGA GAG ATG<br>Arg His Thr Phe Arg Arg Gln Asn Val Arg Glu Glu Pro Arg Glu Met<br>145                 150                 155                 160 | 480 | |
| CCC AGT TTG CCC CGT TCA TCT GAA AAC ATG ATA AGA GAA GAA CAA TTC<br>Pro Ser Leu Pro Arg Ser Ser Glu Asn Met Ile Arg Glu Glu Gln Phe<br>                165                 170                 175 | 528 | |
| CTT GGT AGA AGA AAA CAA CTG GAA GAT TAC TTG ACA AAG ATA CTA AAA<br>Leu Gly Arg Arg Lys Gln Leu Glu Asp Tyr Leu Thr Lys Ile Leu Lys<br>            180                 185                 190 | 576 | |
| ATG CCC ATG TAT AGA AAC TAT CAT GCC ACA ACA GAG TTT CTT GAT ATA<br>Met Pro Met Tyr Arg Asn Tyr His Ala Thr Thr Glu Phe Leu Asp Ile | 624 | |

```
                195                     200                     205
AGC CAG CTG TCT TTC ATC CAT GAT TTG GGA C CA AAG GGC ATA GAA GGT        672
Ser Gln Leu Ser Phe Ile His Asp Leu Gly P ro Lys Gly Ile Glu Gly
        210                     215                 220

ATG ATA ATG AAA AGA TCT GGA GGA CAC AGA A TA CCA GGC TTG AAT TGC        720
Met Ile Met Lys Arg Ser Gly Gly His Arg I le Pro Gly Leu Asn Cys
225                     230                     235                 240

TGT GGT CAG GGA AGA GCC TGC TAC AGA TGG T CA AAA AGA TGG TTA ATA        768
Cys Gly Gln Gly Arg Ala Cys Tyr Arg Trp S er Lys Arg Trp Leu Ile
                245                     250                     255

GTG AAA GAT TCC TTT TTA TTG TAT ATG AAA C CA GAC AGC GGT GCC ATT        816
Val Lys Asp Ser Phe Leu Leu Tyr Met Lys P ro Asp Ser Gly Ala Ile
            260                     265                     270

GCC TTC GTC CTG CTG GTA GAC AAA GAA TTC A AA ATT AAG GTG GGG AAG        864
Ala Phe Val Leu Leu Val Asp Lys Glu Phe L ys Ile Lys Val Gly Lys
        275                     280                     285

AAG GAG ACA GAA ACG AAA TAT GGA ATC CGA A TT GAT AAT CTT TCA AGG        912
Lys Glu Thr Glu Thr Lys Tyr Gly Ile Arg I le Asp Asn Leu Ser Arg
    290                     295                 300

ACA CTT ATT TTA AAA TGC AAC AGC TAT AGA C AT GCT CGG TGG TGG GGA        960
Thr Leu Ile Leu Lys Cys Asn Ser Tyr Arg H is Ala Arg Trp Trp Gly
305                     310                     315                 320

GGG GCT ATA GAA GAA TTC ATC CAG AAA CAT G GC ACC AAC TTT CTC AAA       1008
Gly Ala Ile Glu Glu Phe Ile Gln Lys His G ly Thr Asn Phe Leu Lys
                325                     330                     335

GAT CAT CGA TTT GGG TCA TAT GCT GCT ATC C AA GAG AAT GCT TTA GCT       1056
Asp His Arg Phe Gly Ser Tyr Ala Ala Ile G ln Glu Asn Ala Leu Ala
            340                     345                     350

AAA TGG TAT GTT AAT GCC AAA GGA TAT TTT G AA GAT GTG GCA AAT GCA       1104
Lys Trp Tyr Val Asn Ala Lys Gly Tyr Phe G lu Asp Val Ala Asn Ala
        355                     360                     365

ATG GAA GAG GCA AAT GAA GAG ATT TTT ATC A CA GAC TGG TGG CTG AGT       1152
Met Glu Glu Ala Asn Glu Glu Ile Phe Ile T hr Asp Trp Trp Leu Ser
    370                     375                     380

CCA GAA ATC TTC CTG AAA CGC CCA GTG GTT G AG GGA AAT CGT TGG AGG       1200
Pro Glu Ile Phe Leu Lys Arg Pro Val Val G lu Gly Asn Arg Trp Arg
385                     390                     395                 400

TTG GAC TGC ATT CTT AAA CGA AAA GCA CAA C AA GGA GTG AGG ATC TTC       1248
Leu Asp Cys Ile Leu Lys Arg Lys Ala Gln G ln Gly Val Arg Ile Phe
                405                     410                     415

ATA ATG CTC TAC AAA GAG GTG GAA CTC GCT C TT GGC ATC AAT AGT GAA       1296
Ile Met Leu Tyr Lys Glu Val Glu Leu Ala L eu Gly Ile Asn Ser Glu
            420                     425                     430

TAC ACC AAG AGG ACT TTG ATG CGT CTA CAT C CC AAC ATA AAG GTG ATG       1344
Tyr Thr Lys Arg Thr Leu Met Arg Leu His P ro Asn Ile Lys Val Met
        435                     440                     445

AGA CAC CCG GAT CAT GTG TCA TCC ACC GTC T AT TTG TGG GCT CAC CAT       1392
Arg His Pro Asp His Val Ser Ser Thr Val T yr Leu Trp Ala His His
    450                     455                     460

GAG AAG CTT GTC ATC ATT GAC CAA TCG GTG G CC TTT GTG GGA GGG ATT       1440
Glu Lys Leu Val Ile Ile Asp Gln Ser Val A la Phe Val Gly Gly Ile
465                     470                     475                 480

GAC CTG GCC TAT GGA AGG TGG GAC GAC AAT G AG CAC AGA CTC ACA GAC       1488
Asp Leu Ala Tyr Gly Arg Trp Asp Asp Asn G lu His Arg Leu Thr Asp
                485                     490                     495

GTG GGC AGT GTG AAG CGG GTC ACT TCA GGA C CG TCT CTG GGT CCC CTC       1536
Val Gly Ser Val Lys Arg Val Thr Ser Gly P ro Ser Leu Gly Ser Leu
            500                     505                     510

CCA CCT GCC GCA ATG GAG TCT ATG GAA TCC T TA AGA CTC AAA GAT AAA       1584
```

```
Pro Pro Ala Ala Met Glu Ser Met Glu Ser L eu Arg Leu Lys Asp Lys
        515                 520                 525

AAT GAG CCT GTT CAA AAC CTA CCC ATC CAG A AG AGT ATT GAT GAT GTG      1632
Asn Glu Pro Val Gln Asn Leu Pro Ile Gln L ys Ser Ile Asp Asp Val
    530                 535                 540

GAT TCA AAA CTG AAA GGA ATA GGA AAG CCA A GA AAG TTC TCC AAA TTT      1680
Asp Ser Lys Leu Lys Gly Ile Gly Lys Pro A rg Lys Phe Ser Lys Phe
545                 550                 555                 560

AGT CTC TAC AAG CAG CTC CAC AGG CAC CAC C TG CAC GAC GCA GAT AGC      1728
Ser Leu Tyr Lys Gln Leu His Arg His His L eu His Asp Ala Asp Ser
                565                 570                 575

ATC AGC AGC ATT GAC AGC ACC TCC AAT ACC G GG TCC ATC CGT AGT TTA      1776
Ile Ser Ser Ile Asp Ser Thr Ser Asn Thr G ly Ser Ile Arg Ser Leu
            580                 585                 590

CAG ACA GGT GTG GGA GAG CTG CAT GGG GAA A CC AGA TTC TGG CAT GGA      1824
Gln Thr Gly Val Gly Glu Leu His Gly Glu T hr Arg Phe Trp His Gly
        595                 600                 605

AAG GAC TAC TGC AAT TTC GTC TTC AAA GAC T GG GTT CAA CTT GAT AAA      1872
Lys Asp Tyr Cys Asn Phe Val Phe Lys Asp T rp Val Gln Leu Asp Lys
    610                 615                 620

CCT TTT GCT GAT TTC ATT GAC AGG TAC TCC A CG CCC CGG ATG CCC TGG      1920
Pro Phe Ala Asp Phe Ile Asp Arg Tyr Ser T hr Pro Arg Met Pro Trp
625                 630                 635                 640

CAT GAC ATT GCC TCT GCA GTC CAC GGG AAG G CG GCT CGT GAT GTG GCA      1968
His Asp Ile Ala Ser Ala Val His Gly Lys A la Ala Arg Asp Val Ala
                645                 650                 655

CGT CAC TTC ATC CAG CGC TGG AAC TTC ACA A AA ATT ATG AAA TCA AAA      2016
Arg His Phe Ile Gln Arg Trp Asn Phe Thr L ys Ile Met Lys Ser Lys
            660                 665                 670

TAT CGG TCC CTT TCT TAT CCT TTT CTG CTT C CA AAG TCT CAA ACA ACA      2064
Tyr Arg Ser Leu Ser Tyr Pro Phe Leu Leu P ro Lys Ser Gln Thr Thr
        675                 680                 685

GCC CAT GAG TTG AGA TAT CAA GTG CCT GGG T CT GTC CAT GCT AAC GTA      2112
Ala His Glu Leu Arg Tyr Gln Val Pro Gly S er Val His Ala Asn Val
    690                 695                 700

CAG TTG CTC CGC TCT GCT GCT GAT TGG TCT G CT GGT ATA AAG TAC CAT      2160
Gln Leu Leu Arg Ser Ala Ala Asp Trp Ser A la Gly Ile Lys Tyr His
705                 710                 715                 720

GAA GAG TCC ATC CAC GCC GCT TAC GTC CAT G TG ATA GAG AAC AGC AGG      2208
Glu Glu Ser Ile His Ala Ala Tyr Val His V al Ile Glu Asn Ser Arg
                725                 730                 735

CAC TAT ATC TAT ATC GAA AAC CAG TTT TTC A TA AGC TGT GCT GAT GAC      2256
His Tyr Ile Tyr Ile Glu Asn Gln Phe Phe I le Ser Cys Ala Asp Asp
            740                 745                 750

AAA GTT GTG TTC AAC AAG ATA GGC GAT GCC A TT GCC CAG AGG ATC CTG      2304
Lys Val Val Phe Asn Lys Ile Gly Asp Ala I le Ala Gln Arg Ile Leu
        755                 760                 765

AAA GCT CAC AGG GAA AAC CAG AAA TAC CGG G TA TAT GTC GTG ATA CCA      2352
Lys Ala His Arg Glu Asn Gln Lys Tyr Arg V al Tyr Val Val Ile Pro
    770                 775                 780

CTT CTG CCA GGG TTC GAA GGA GAC ATT TCA A CC GGC GGA GGA AAT GCT      2400
Leu Leu Pro Gly Phe Glu Gly Asp Ile Ser T hr Gly Gly Gly Asn Ala
785                 790                 795                 800

CTA CAG GCA ATC ATG CAC TTC AAC TAC AGA A CC ATG TGC AGA GGA GAA      2448
Leu Gln Ala Ile Met His Phe Asn Tyr Arg T hr Met Cys Arg Gly Glu
                805                 810                 815

AAT TCC ATC CTT GGA CAG TTA AAA GCA GAG C TT GGT AAT CAG TGG ATA      2496
Asn Ser Ile Leu Gly Gln Leu Lys Ala Glu L eu Gly Asn Gln Trp Ile
            820                 825                 830
```

```
AAT TAC ATA TCA TTC TGT GGT CTT AGA ACA C AT GCA GAG CTC GAA GGA         2544
Asn Tyr Ile Ser Phe Cys Gly Leu Arg Thr H is Ala Glu Leu Glu Gly
            835                 840                 845

AAC CTA GTA ACT GAG CTT ATC TAT GTC CAC A GC AAG TTG TTA ATT GCT         2592
Asn Leu Val Thr Glu Leu Ile Tyr Val His S er Lys Leu Leu Ile Ala
        850                 855                 860

GAT GAT AAC ACT GTT ATT ATT GGC TCT GCC A AC ATA AAT GAC CGC AGC         2640
Asp Asp Asn Thr Val Ile Ile Gly Ser Ala A sn Ile Asn Asp Arg Ser
865                 870                 875                 880

ATG CTG GGA AAG CGT GAC AGT GAA ATG GCT G TC ATT GTG CAA GAT ACA         2688
Met Leu Gly Lys Arg Asp Ser Glu Met Ala V al Ile Val Gln Asp Thr
                885                 890                 895

GAG ACT GTT CCT TCA GTA ATG GAT GGA AAA G AG TAC CAA GCT GGC CGG         2736
Glu Thr Val Pro Ser Val Met Asp Gly Lys G lu Tyr Gln Ala Gly Arg
            900                 905                 910

TTT GCC CGA GGA CTT CGG CTA CAG TGC TTT A GG GTT GTC CTT GGC TAT         2784
Phe Ala Arg Gly Leu Arg Leu Gln Cys Phe A rg Val Val Leu Gly Tyr
        915                 920                 925

CTT GAT GAC CCA AGT GAG GAC ATT CAG GAT C CA GTG AGT GAC AAA TTC         2832
Leu Asp Asp Pro Ser Glu Asp Ile Gln Asp P ro Val Ser Asp Lys Phe
    930                 935                 940

TTC AAG GAG GTG TGG GTT TCA ACA GCA GCT C GA AAT GCT ACA ATT TAT         2880
Phe Lys Glu Val Trp Val Ser Thr Ala Ala A rg Asn Ala Thr Ile Tyr
945                 950                 955                 960

GAC AAG GTT TTC CGG TGC CTT CCC AAT GAT G AA GTA CAC AAT TTA ATT         2928
Asp Lys Val Phe Arg Cys Leu Pro Asn Asp G lu Val His Asn Leu Ile
                965                 970                 975

CAG CTG AGA GAC TTT ATA AAC AAG CCC GTA T TA GCT AAG GAA GAT CCC         2976
Gln Leu Arg Asp Phe Ile Asn Lys Pro Val L eu Ala Lys Glu Asp Pro
            980                 985                 990

ATT CGA GCT GAG GAG GAA CTG AAG AAG ATC C GT GGA TTT TTG GTG CAA         3024
Ile Arg Ala Glu Glu Glu Leu Lys Lys Ile A rg Gly Phe Leu Val Gln
        995                 1000                1005

TTC CCC TTT TAT TTC TTG TCT GAA GAA AGC C TA CTG CCT TCT GTT GGG         3072
Phe Pro Phe Tyr Phe Leu Ser Glu Glu Ser L eu Leu Pro Ser Val Gly
    1010                1015                1020

ACC AAA GAG GCC ATA GTG CCC ATG GAG GTT T GG ACT                         3108
Thr Lys Glu Ala Ile Val Pro Met Glu Val T rp Thr
1025                1030                1035

(2) INFORMATION FOR SEQ ID NO:4:

(i) SEQUENCE CHARACTERISTICS:
        (A) LENGTH: 1036 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Leu Lys Asn Glu Pro Arg Val Asn T hr Ser Ala Leu Gln Lys
1               5                   10                  15

Ile Ala Ala Asp Met Ser Asn Ile Ile Glu A sn Leu Asp Thr Arg Glu
                20                  25                  30

Leu His Phe Glu Gly Glu Glu Val Asp Tyr A sp Val Ser Pro Ser Asp
            35                  40                  45

Pro Lys Ile Gln Glu Val Tyr Ile Pro Phe S er Ala Ile Tyr Asn Thr
        50                  55                  60

Gln Gly Phe Lys Glu Pro Asn Ile Gln Thr T yr Leu Ser Gly Cys Pro
65                  70                  75                  80
```

```
Ile Lys Ala Gln Val Leu Glu Val Arg Phe Thr Ser Thr Thr Arg
                85                  90                  95

Val Pro Ser Ile Asn Leu Tyr Thr Ile Glu Leu Thr His Gly Glu Phe
            100                 105                 110

Lys Trp Gln Val Lys Arg Lys Phe Lys His Phe Gln Glu Phe His Arg
            115                 120                 125

Glu Leu Leu Lys Tyr Lys Ala Phe Ile Arg Ile Pro Ile Pro Thr Arg
    130                 135                 140

Arg His Thr Phe Arg Arg Gln Asn Val Arg Glu Glu Pro Arg Glu Met
145                 150                 155                 160

Pro Ser Leu Pro Arg Ser Ser Glu Asn Met Ile Arg Glu Glu Gln Phe
                165                 170                 175

Leu Gly Arg Arg Lys Gln Leu Glu Asp Tyr Leu Thr Lys Ile Leu Lys
            180                 185                 190

Met Pro Met Tyr Arg Asn Tyr His Ala Thr Thr Glu Phe Leu Asp Ile
            195                 200                 205

Ser Gln Leu Ser Phe Ile His Asp Leu Gly Pro Lys Gly Ile Glu Gly
    210                 215                 220

Met Ile Met Lys Arg Ser Gly Gly His Arg Ile Pro Gly Leu Asn Cys
225                 230                 235                 240

Cys Gly Gln Gly Arg Ala Cys Tyr Arg Trp Ser Lys Arg Trp Leu Ile
                245                 250                 255

Val Lys Asp Ser Phe Leu Leu Tyr Met Lys Pro Asp Ser Gly Ala Ile
            260                 265                 270

Ala Phe Val Leu Leu Val Asp Lys Glu Phe Lys Ile Lys Val Gly Lys
    275                 280                 285

Lys Glu Thr Glu Thr Lys Tyr Gly Ile Arg Ile Asp Asn Leu Ser Arg
290                 295                 300

Thr Leu Ile Leu Lys Cys Asn Ser Tyr Arg His Ala Arg Trp Trp Gly
305                 310                 315                 320

Gly Ala Ile Glu Glu Phe Ile Gln Lys His Gly Thr Asn Phe Leu Lys
                325                 330                 335

Asp His Arg Phe Gly Ser Tyr Ala Ala Ile Gln Glu Asn Ala Leu Ala
            340                 345                 350

Lys Trp Tyr Val Asn Ala Lys Gly Tyr Phe Glu Asp Val Ala Asn Ala
    355                 360                 365

Met Glu Glu Ala Asn Glu Glu Ile Phe Ile Thr Asp Trp Trp Leu Ser
370                 375                 380

Pro Glu Ile Phe Leu Lys Arg Pro Val Val Glu Gly Asn Arg Trp Arg
385                 390                 395                 400

Leu Asp Cys Ile Leu Lys Arg Lys Ala Gln Gly Val Arg Ile Phe
                405                 410                 415

Ile Met Leu Tyr Lys Glu Val Glu Leu Ala Leu Gly Ile Asn Ser Glu
            420                 425                 430

Tyr Thr Lys Arg Thr Leu Met Arg Leu His Pro Asn Ile Lys Val Met
    435                 440                 445

Arg His Pro Asp His Val Ser Ser Thr Val Tyr Leu Trp Ala His His
450                 455                 460

Glu Lys Leu Val Ile Ile Asp Gln Ser Val Ala Phe Val Gly Gly Ile
465                 470                 475                 480

Asp Leu Ala Tyr Gly Arg Trp Asp Asp Asn Glu His Arg Leu Thr Asp
                485                 490                 495

Val Gly Ser Val Lys Arg Val Thr Ser Gly Pro Ser Leu Gly Ser Leu
```

-continued

```
                500                 505                 510
Pro Pro Ala Ala Met Glu Ser Met Glu Ser L eu Arg Leu Lys Asp Lys
        515                 520                 525

Asn Glu Pro Val Gln Asn Leu Pro Ile Gln L ys Ser Ile Asp Asp Val
530                 535                 540

Asp Ser Lys Leu Lys Gly Ile Gly Lys Pro A rg Lys Phe Ser Lys Phe
545                 550                 555                 560

Ser Leu Tyr Lys Gln Leu His Arg His His L eu His Asp Ala Asp Ser
            565                 570                 575

Ile Ser Ser Ile Asp Ser Thr Ser Asn Thr G ly Ser Ile Arg Ser Leu
            580                 585                 590

Gln Thr Gly Val Gly Glu Leu His Gly Glu T hr Arg Phe Trp His Gly
        595                 600                 605

Lys Asp Tyr Cys Asn Phe Val Phe Lys Asp T rp Val Gln Leu Asp Lys
        610                 615                 620

Pro Phe Ala Asp Phe Ile Asp Arg Tyr Ser T hr Pro Arg Met Pro Trp
625                 630                 635                 640

His Asp Ile Ala Ser Ala Val His Gly Lys A la Ala Arg Asp Val Ala
            645                 650                 655

Arg His Phe Ile Gln Arg Trp Asn Phe Thr L ys Ile Met Lys Ser Lys
            660                 665                 670

Tyr Arg Ser Leu Ser Tyr Pro Phe Leu Leu P ro Lys Ser Gln Thr Thr
            675                 680                 685

Ala His Glu Leu Arg Tyr Gln Val Pro Gly S er Val His Ala Asn Val
        690                 695                 700

Gln Leu Leu Arg Ser Ala Ala Asp Trp Ser A la Gly Ile Lys Tyr His
705                 710                 715                 720

Glu Glu Ser Ile His Ala Ala Tyr Val His V al Ile Glu Asn Ser Arg
            725                 730                 735

His Tyr Ile Tyr Ile Glu Asn Gln Phe Phe I le Ser Cys Ala Asp Asp
            740                 745                 750

Lys Val Val Phe Asn Lys Ile Gly Asp Ala I le Ala Gln Arg Ile Leu
            755                 760                 765

Lys Ala His Arg Glu Asn Gln Lys Tyr Arg V al Tyr Val Val Ile Pro
        770                 775                 780

Leu Leu Pro Gly Phe Glu Gly Asp Ile Ser T hr Gly Gly Gly Asn Ala
785                 790                 795                 800

Leu Gln Ala Ile Met His Phe Asn Tyr Arg T hr Met Cys Arg Gly Glu
            805                 810                 815

Asn Ser Ile Leu Gly Gln Leu Lys Ala Glu L eu Gly Asn Gln Trp Ile
            820                 825                 830

Asn Tyr Ile Ser Phe Cys Gly Leu Arg Thr H is Ala Glu Leu Glu Gly
            835                 840                 845

Asn Leu Val Thr Glu Leu Ile Tyr Val His S er Lys Leu Leu Ile Ala
        850                 855                 860

Asp Asp Asn Thr Val Ile Ile Gly Ser Ala A sn Ile Asn Asp Arg Ser
865                 870                 875                 880

Met Leu Gly Lys Arg Asp Ser Glu Met Ala V al Ile Val Gln Asp Thr
            885                 890                 895

Glu Thr Val Pro Ser Val Met Asp Gly Lys G lu Tyr Gln Ala Gly Arg
        900                 905                 910

Phe Ala Arg Gly Leu Arg Leu Gln Cys Phe A rg Val Val Leu Gly Tyr
        915                 920                 925
```

```
Leu Asp Asp Pro Ser Glu Asp Ile Gln Asp Pro Val Ser Asp Lys Phe
    930                 935                 940

Phe Lys Glu Val Trp Val Ser Thr Ala Ala Arg Asn Ala Thr Ile Tyr
945                 950                 955                 960

Asp Lys Val Phe Arg Cys Leu Pro Asn Asp Glu Val His Asn Leu Ile
                965                 970                 975

Gln Leu Arg Asp Phe Ile Asn Lys Pro Val Leu Ala Lys Glu Asp Pro
            980                 985                 990

Ile Arg Ala Glu Glu Leu Lys Lys Ile Arg Gly Phe Leu Val Gln
        995                 1000                1005

Phe Pro Phe Tyr Phe Leu Ser Glu Ser Leu Leu Pro Ser Val Gly
    1010                1015                1020

Thr Lys Glu Ala Ile Val Pro Met Glu Val Trp Thr
1025                1030                1035

(2) INFORMATION FOR SEQ ID NO:5:

(i) SEQUENCE CHARACTERISTICS:
        (A) LENGTH: 2799 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..2799

(xi) SEQUENCE DESCRIPTION: SEQ ID NO:5:

ATG ACT GTA ACC CAG AAG AAC CTC TTT CCC TAT GGG GAC TAT CTG AAC        48
Met Thr Val Thr Gln Lys Asn Leu Phe Pro Tyr Gly Asp Tyr Leu Asn
1               5                   10                  15

TCC AGC CAG TTG CAC ATG GAG CCA GAT GAG GTT GAC ACT CTG AGG GAA        96
Ser Ser Gln Leu His Met Glu Pro Asp Glu Val Asp Thr Leu Arg Glu
                20                  25                  30

GGA GAG GAT CCA GCT GAT CGA ATG CAT CCC TAT CTG GCC ATC TAT GAC       144
Gly Glu Asp Pro Ala Asp Arg Met His Pro Tyr Leu Ala Ile Tyr Asp
            35                  40                  45

CTT CAG CCT CTG AAA GCA CAC CCC TTG GTG TTC GCC CCT GGG GTC CCT       192
Leu Gln Pro Leu Lys Ala His Pro Leu Val Phe Ala Pro Gly Val Pro
        50                  55                  60

GTT ATA GCC CAG GTG GTG GGC ACC GAA AGA TAC ACC AGC GGA TCC AAG       240
Val Ile Ala Gln Val Val Gly Thr Glu Arg Tyr Thr Ser Gly Ser Lys
65                  70                  75                  80

GTG GGA ACC TGT ACT CTA TAT TCT GTT CGC TTG ACG CAT GGT GAC TTT       288
Val Gly Thr Cys Thr Leu Tyr Ser Val Arg Leu Thr His Gly Asp Phe
                85                  90                  95

ACC TGG ACA ACC AAG AAG AAG TTC CGA CAC TTT CAG GAG CTG CAT CGG       336
Thr Trp Thr Thr Lys Lys Lys Phe Arg His Phe Gln Glu Leu His Arg
            100                 105                 110

GAC CTC CAG AGA CAC AAA GTC TTG ATG AGT CTG CTC CCT TTG GCT CGC       384
Asp Leu Gln Arg His Lys Val Leu Met Ser Leu Leu Pro Leu Ala Arg
        115                 120                 125

TTT GCT GTG ACC CAT TCT CCA GCC CGA GAG GCA GCC GCC GAG GAT ATA       432
Phe Ala Val Thr His Ser Pro Ala Arg Glu Ala Ala Ala Glu Asp Ile
    130                 135                 140
```

```
CCC TCC CTA CCC CGA GGA GGT TCT GAG GGC T CT GCC AGA CAC ACA GCC      480
Pro Ser Leu Pro Arg Gly Gly Ser Glu Gly S er Ala Arg His Thr Ala
145                 150                 155                 160

AGC AAA CAG AAA TAC TTG GAA AAT TAC CTC A AC CGC CTC CTG ACC ATG      528
Ser Lys Gln Lys Tyr Leu Glu Asn Tyr Leu A sn Arg Leu Leu Thr Met
                165                 170                 175

TCT TTC TAT CGC AAT TAC CAC GCC ATG ACA G AA TTT CTG GAA GTC AGT      576
Ser Phe Tyr Arg Asn Tyr His Ala Met Thr G lu Phe Leu Glu Val Ser
            180                 185                 190

CAA CTT TCC TTT ATC CCA GAC CTT GGC TCC A AA GGA CTG GAA GGG GTG      624
Gln Leu Ser Phe Ile Pro Asp Leu Gly Ser L ys Gly Leu Glu Gly Val
        195                 200                 205

ATC CGG AAG CGC TCG GGC GGG CAT CGA GTT C CC GGC TTC ACC TTC TGT      672
Ile Arg Lys Arg Ser Gly Gly His Arg Val P ro Gly Phe Thr Phe Cys
210                 215                 220

GGC CGA GAC CAA GTT TGT TAT CGA TGG TCC A AG AGG TGG CTG GTG GTG      720
Gly Arg Asp Gln Val Cys Tyr Arg Trp Ser L ys Arg Trp Leu Val Val
225                 230                 235                 240

AAG GAC TCC TTC CTG CTG TAC ATG CGC CCG G AG ACC GGC GCC ATC TCA      768
Lys Asp Ser Phe Leu Leu Tyr Met Arg Pro G lu Thr Gly Ala Ile Ser
                245                 250                 255

TTT GTT CAG CTT TTT GAC CCT GGC TTT GAG G TC CAG GTC GGA AAA AGG      816
Phe Val Gln Leu Phe Asp Pro Gly Phe Glu V al Gln Val Gly Lys Arg
            260                 265                 270

AGC ACA GAG ACG CGG TAT GGG GTG AGG ATC G AC ACC TCC CAC AGG TCC      864
Ser Thr Glu Thr Arg Tyr Gly Val Arg Ile A sp Thr Ser His Arg Ser
        275                 280                 285

CTG ATT CTC AAA TGC AGC AGC TAC CGG CAG G CA CGG TGG TGG GGC CAG      912
Leu Ile Leu Lys Cys Ser Ser Tyr Arg Gln A la Arg Trp Trp Gly Gln
290                 295                 300

GAG ATC ACG GAG CTG GCA CAG GGT TCG GGC A GA GAT TTT CTA CAG CTA      960
Glu Ile Thr Glu Leu Ala Gln Gly Ser Gly A rg Asp Phe Leu Gln Leu
305                 310                 315                 320

CAT CAG CAT GAC AGC TAT GCC CCA CCC CGG C CC GGC ACC CTG GCC CGG     1008
His Gln His Asp Ser Tyr Ala Pro Pro Arg P ro Gly Thr Leu Ala Arg
                325                 330                 335

TGG TTT GTG AAT GGG GCA GGT TAC TTT GCT G CT GTG GCA GAT GCC ATC     1056
Trp Phe Val Asn Gly Ala Gly Tyr Phe Ala A la Val Ala Asp Ala Ile
            340                 345                 350

CTG CGA GCT CAA GAG GAG ATT TTC ATC ACA G AC TGG TGG TTG AGT CCT     1104
Leu Arg Ala Gln Glu Glu Ile Phe Ile Thr A sp Trp Trp Leu Ser Pro
        355                 360                 365

GAA ATT TAC CTG AAG CGT CCA GCC CAT TCC G AC GAC TGG AGA CTG GAC     1152
Glu Ile Tyr Leu Lys Arg Pro Ala His Ser A sp Asp Trp Arg Leu Asp
370                 375                 380

ATT ATG CTC AAG AGG AAG GCG GAA GAA GGT G TC CGA GTT TCC ATA CTG     1200
Ile Met Leu Lys Arg Lys Ala Glu Glu Gly V al Arg Val Ser Ile Leu
385                 390                 395                 400

CTG TTT AAG GAA GTG GAG CTG GCC TTG GGC A TC AAC AGT GGC TAC AGC     1248
Leu Phe Lys Glu Val Glu Leu Ala Leu Gly I le Asn Ser Gly Tyr Ser
                405                 410                 415

AAG AGG ACG CTG ATG CTG CTG CAT CCC AAC A TA AAG GTG ATG CGA CAC     1296
Lys Arg Thr Leu Met Leu Leu His Pro Asn I le Lys Val Met Arg His
            420                 425                 430

CCA GAC CTT GTG ACA CTG TGG GCT CAT CAC G AG AAG CTC CTG GTG GTA     1344
Pro Asp Leu Val Thr Leu Trp Ala His His G lu Lys Leu Leu Val Val
        435                 440                 445

GAC CAA GTG GTG GCA TTC TTG GGC GGG CTG G AC CTG GCC TTC GGC CGC     1392
Asp Gln Val Val Ala Phe Leu Gly Gly Leu A sp Leu Ala Phe Gly Arg
450                 455                 460
```

```
TGG GAT GAC GTG CAA TAC CGA CTG ACT GAC C TG GGT GAC CCC TCT GAA       1440
Trp Asp Asp Val Gln Tyr Arg Leu Thr Asp L eu Gly Asp Pro Ser Glu
465                     470                 475                 480

CCT GTA CAT TTA CAG ACT CCC ACA CTA GGT T CA GAC CCT GCA GCC ACT       1488
Pro Val His Leu Gln Thr Pro Thr Leu Gly S er Asp Pro Ala Ala Thr
                    485                 490                 495

CCA GAC CTC TCG CAT AAC CAA TTC TTC TGG C TG GGA AAG GAC TAC AGC       1536
Pro Asp Leu Ser His Asn Gln Phe Phe Trp L eu Gly Lys Asp Tyr Ser
                500                 505                 510

AAC CTC ATC ACC AAG GAC TGG GTG CAG CTG G AC CGG CCT TTT GAA GAT       1584
Asn Leu Ile Thr Lys Asp Trp Val Gln Leu A sp Arg Pro Phe Glu Asp
            515                 520                 525

TTC ATC GAC AGG GAG ACC ACA CCC AGG ATG C CA TGG AGG GAT GTT GGA       1632
Phe Ile Asp Arg Glu Thr Thr Pro Arg Met P ro Trp Arg Asp Val Gly
530                 535                 540

GTG GTT GTA CAC GGA GTA GCT GCC AGG GAC C TT GCC CGG CAC TTC ATC       1680
Val Val Val His Gly Val Ala Ala Arg Asp L eu Ala Arg His Phe Ile
545                 550                 555                 560

CAG CGC TGG AAT TTC ACC AAG ACC ACC AAG G CC AGG TAT AAG ACA CCT       1728
Gln Arg Trp Asn Phe Thr Lys Thr Thr Lys A la Arg Tyr Lys Thr Pro
                565                 570                 575

TTG TAC CCC TAC CTG CTG CCC AAG TCC ACC A GC ACT GCA AAC AAT CTC       1776
Leu Tyr Pro Tyr Leu Leu Pro Lys Ser Thr S er Thr Ala Asn Asn Leu
                580                 585                 590

CCC TTC ATG ATC CCA GGC GGG CAG TGT GCC A CT GTG CAG GTC TTG AGG       1824
Pro Phe Met Ile Pro Gly Gly Gln Cys Ala T hr Val Gln Val Leu Arg
            595                 600                 605

TCT GTG GAT CGA TGG TCA GCA GGG ACA TTG G AG AAC TCC ATC CTC AAT       1872
Ser Val Asp Arg Trp Ser Ala Gly Thr Leu G lu Asn Ser Ile Leu Asn
610                 615                 620

GCC TAC CTA CAT ACC ATT CGA GAG AGC CAG C AC TTT CTC TAC ATT GAG       1920
Ala Tyr Leu His Thr Ile Arg Glu Ser Gln H is Phe Leu Tyr Ile Glu
625                 630                 635                 640

AAT CAG TTC TTC ATT AGC TGC TCA GAT GGG C GA ACA GTT CTG AAC AAG       1968
Asn Gln Phe Phe Ile Ser Cys Ser Asp Gly A rg Thr Val Leu Asn Lys
                645                 650                 655

GTG GGC GAT GAG ATT GTG GAC AGA ATC CTG A AG GCT CAC GAA CAG GGG       2016
Val Gly Asp Glu Ile Val Asp Arg Ile Leu L ys Ala His Glu Gln Gly
                660                 665                 670

CAG TGT TTC CGA GTC TAC TTG CTT CTG CCT T TG CTC CCT GGC TTT GAG       2064
Gln Cys Phe Arg Val Tyr Leu Leu Leu Pro L eu Leu Pro Gly Phe Glu
            675                 680                 685

GGG GAC ATC TCC ACA GGG GGT GGT AAC TCC A TC CAG GCT ATT CTG CAC       2112
Gly Asp Ile Ser Thr Gly Gly Gly Asn Ser I le Gln Ala Ile Leu His
690                 695                 700

TTC ACC TAC AGG ACC CTG TGT CGT GGG GAA C AT TCA ATC CTA CAT CGT       2160
Phe Thr Tyr Arg Thr Leu Cys Arg Gly Glu H is Ser Ile Leu His Arg
705                 710                 715                 720

CTC AAA GCA GCC ATG GGG ACT GCG TGG CGA G AT TAC ATG TCC ATC TGT       2208
Leu Lys Ala Ala Met Gly Thr Ala Trp Arg A sp Tyr Met Ser Ile Cys
                725                 730                 735

GGG CTT CGC ACC CAT GGA GAG CTG GGC GGG C AC CCA ATC TCT GAG CTC       2256
Gly Leu Arg Thr His Gly Glu Leu Gly Gly H is Pro Ile Ser Glu Leu
                740                 745                 750

ATC TAT ATC CAC AGC AAG ATG CTC ATT GCG G AT GAC AGA ACA GTC ATC       2304
Ile Tyr Ile His Ser Lys Met Leu Ile Ala A sp Asp Arg Thr Val Ile
            755                 760                 765

ATT GGT TCT GCG AAC ATC AAT GAC AGG AGC T TG CTG GGG AAG CGT GAC       2352
Ile Gly Ser Ala Asn Ile Asn Asp Arg Ser L eu Leu Gly Lys Arg Asp
```

```
                770              775              780
AGT GAG CTA GCC ATC CTG ATC AAG GAC ACA G AA ATG GAA CCA TCC CTC                2400
Ser Glu Leu Ala Ile Leu Ile Lys Asp Thr G lu Met Glu Pro Ser Leu
785                 790              795                   800

ATG GAT GGG GTG GAG TAC CAG GCA GGC AGA T TT GCC TTG AGT TTG CGG                2448
Met Asp Gly Val Glu Tyr Gln Ala Gly Arg P he Ala Leu Ser Leu Arg
                805              810              815

GGA AGA TGT TTC AGT GTG ATT CTT GGG GCA A AT ACC TGG CCA GAC CTG                2496
Gly Arg Cys Phe Ser Val Ile Leu Gly Ala A sn Thr Trp Pro Asp Leu
            820              825              830

GAT CTC CGA GAC CCT GTC TGT GAT GAC TTC T TC CAG CTG TGG CAA GAA                2544
Asp Leu Arg Asp Pro Val Cys Asp Asp Phe P he Gln Leu Trp Gln Glu
            835              840              845

ACA GCG GAG AAC AAT GCC ACC ATC TAT GAG C AG ATC TTC CGC TGC CTG                2592
Thr Ala Glu Asn Asn Ala Thr Ile Tyr Glu G ln Ile Phe Arg Cys Leu
850              855              860

CCG TCC AAT GCT ACC CGT TCC CTG CGG CTC T CC GGG AGT ATG TGG CTG                2640
Pro Ser Asn Ala Thr Arg Ser Leu Arg Leu S er Gly Ser Met Trp Leu
865              870              875              880

TGG AGT CCT TGG CTA CAG TCA GCC TTC TTG G CT CAG TCT GAG CTT GCC                2688
Trp Ser Pro Trp Leu Gln Ser Ala Phe Leu A la Gln Ser Glu Leu Ala
                885              890              895

CAC ATC CAG GGC CAC CTA GTT CAC TTC CCC C TC AAG TTT CTG GAG GAC                2736
His Ile Gln Gly His Leu Val His Phe Pro L eu Lys Phe Leu Glu Asp
                900              905              910

GAG TCC TTG TTG CCC CCA CTG GGG AGT AAA G AA GGG ATG ATA CCT TTA                2784
Glu Ser Leu Leu Pro Pro Leu Gly Ser Lys G lu Gly Met Ile Pro Leu
            915              920              925

GAA GTG TGG ACA TAG                                                             2799
Glu Val Trp Thr *
930

(2) INFORMATION FOR SEQ ID NO:6:

(i) SEQUENCE CHARACTERISTICS:
        (A) LENGTH: 932 am ino acids
        (B) TYPE: amino acid
        (D) TOPOLOGY: linear (ii) MOLECULE TYPE: protein (xi) SEQUENCE DESCRIPTION: SEQ ID NO:6:

Met Thr Val Thr Gln Lys Asn Leu Phe Pro T yr Gly Asp Tyr Leu Asn
 1               5                  10                  15

Ser Ser Gln Leu His Met Glu Pro Asp Glu V al Asp Thr Leu Arg Glu
             20                  25                  30

Gly Glu Asp Pro Ala Asp Arg Met His Pro T yr Leu Ala Ile Tyr Asp
         35                  40                  45

Leu Gln Pro Leu Lys Ala His Pro Leu Val P he Ala Pro Gly Val Pro
     50                  55                  60

Val Ile Ala Gln Val Val Gly Thr Glu Arg T yr Thr Ser Gly Ser Lys
65                  70                  75                  80

Val Gly Thr Cys Thr Leu Tyr Ser Val Arg L eu Thr His Gly Asp Phe
                 85                  90                  95

Thr Trp Thr Thr Lys Lys Phe Arg His P he Gln Glu Leu His Arg
             100                 105                 110

Asp Leu Gln Arg His Lys Val Leu Met Ser L eu Leu Pro Leu Ala Arg
         115                 120                 125

Phe Ala Val Thr His Ser Pro Ala Arg Glu A la Ala Ala Glu Asp Ile
```

```
                130               135               140
Pro Ser Leu Pro Arg Gly Gly Ser Glu Gly S er Ala Arg His Thr Ala
145               150               155               160
Ser Lys Gln Lys Tyr Leu Glu Asn Tyr Leu A sn Arg Leu Leu Thr Met
                165               170               175
Ser Phe Tyr Arg Asn Tyr His Ala Met Thr G lu Phe Leu Glu Val Ser
                180               185               190
Gln Leu Ser Phe Ile Pro Asp Leu Gly Ser L ys Gly Leu Glu Gly Val
                195               200               205
Ile Arg Lys Arg Ser Gly Gly His Arg Val P ro Gly Phe Thr Phe Cys
210               215               220
Gly Arg Asp Gln Val Cys Tyr Arg Trp Ser L ys Arg Trp Leu Val Val
225               230               235               240
Lys Asp Ser Phe Leu Leu Tyr Met Arg Pro G lu Thr Gly Ala Ile Ser
                245               250               255
Phe Val Gln Leu Phe Asp Pro Gly Phe Glu V al Gln Val Gly Lys Arg
                260               265               270
Ser Thr Glu Thr Arg Tyr Gly Val Arg Ile A sp Thr Ser His Arg Ser
                275               280               285
Leu Ile Leu Lys Cys Ser Ser Tyr Arg Gln A la Arg Trp Trp Gly Gln
                290               295               300
Glu Ile Thr Glu Leu Ala Gln Gly Ser Gly A rg Asp Phe Leu Gln Leu
305               310               315               320
His Gln His Asp Ser Tyr Ala Pro Pro Arg P ro Gly Thr Leu Ala Arg
                325               330               335
Trp Phe Val Asn Gly Ala Gly Tyr Phe Ala A la Val Ala Asp Ala Ile
                340               345               350
Leu Arg Ala Gln Glu Glu Ile Phe Ile Thr A sp Trp Trp Leu Ser Pro
                355               360               365
Glu Ile Tyr Leu Lys Arg Pro Ala His Ser A sp Asp Trp Arg Leu Asp
370               375               380
Ile Met Leu Lys Arg Lys Ala Glu Glu Gly V al Arg Val Ser Ile Leu
385               390               395               400
Leu Phe Lys Glu Val Glu Leu Ala Leu Gly I le Asn Ser Gly Tyr Ser
                405               410               415
Lys Arg Thr Leu Met Leu Leu His Pro Asn I le Lys Val Met Arg His
                420               425               430
Pro Asp Leu Val Thr Leu Trp Ala His His G lu Lys Leu Leu Val Val
                435               440               445
Asp Gln Val Val Ala Phe Leu Gly Gly Leu A sp Leu Ala Phe Gly Arg
                450               455               460
Trp Asp Asp Val Gln Tyr Arg Leu Thr Asp L eu Gly Asp Pro Ser Glu
465               470               475               480
Pro Val His Leu Gln Thr Pro Thr Leu Gly S er Asp Pro Ala Ala Thr
                485               490               495
Pro Asp Leu Ser His Asn Gln Phe Phe Trp L eu Gly Lys Asp Tyr Ser
                500               505               510
Asn Leu Ile Thr Lys Asp Trp Val Gln Leu A sp Arg Pro Phe Glu Asp
                515               520               525
Phe Ile Asp Arg Glu Thr Thr Pro Arg Met P ro Trp Arg Asp Val Gly
                530               535               540
Val Val Val His Gly Val Ala Ala Arg Asp L eu Ala Arg His Phe Ile
545               550               555               560
```

```
Gln Arg Trp Asn Phe Thr Lys Thr Thr Lys Ala Arg Tyr Lys Thr Pro
                565                 570                 575

Leu Tyr Pro Tyr Leu Leu Pro Lys Ser Thr Ser Thr Ala Asn Asn Leu
            580                 585                 590

Pro Phe Met Ile Pro Gly Gly Gln Cys Ala Thr Val Gln Val Leu Arg
        595                 600                 605

Ser Val Asp Arg Trp Ser Ala Gly Thr Leu Glu Asn Ser Ile Leu Asn
610                 615                 620

Ala Tyr Leu His Thr Ile Arg Glu Ser Gln His Phe Leu Tyr Ile Glu
625                 630                 635                 640

Asn Gln Phe Phe Ile Ser Cys Ser Asp Gly Arg Thr Val Leu Asn Lys
                645                 650                 655

Val Gly Asp Glu Ile Val Asp Arg Ile Leu Lys Ala His Glu Gln Gly
                660                 665                 670

Gln Cys Phe Arg Val Tyr Leu Leu Pro Leu Leu Pro Gly Phe Glu
            675                 680                 685

Gly Asp Ile Ser Thr Gly Gly Gly Asn Ser Ile Gln Ala Ile Leu His
690                 695                 700

Phe Thr Tyr Arg Thr Leu Cys Arg Gly Glu His Ser Ile Leu His Arg
705                 710                 715                 720

Leu Lys Ala Ala Met Gly Thr Ala Trp Arg Asp Tyr Met Ser Ile Cys
                725                 730                 735

Gly Leu Arg Thr His Gly Glu Leu Gly Gly His Pro Ile Ser Glu Leu
                740                 745                 750

Ile Tyr Ile His Ser Lys Met Leu Ile Ala Asp Asp Arg Thr Val Ile
                755                 760                 765

Ile Gly Ser Ala Asn Ile Asn Asp Arg Ser Leu Leu Gly Lys Arg Asp
770                 775                 780

Ser Glu Leu Ala Ile Leu Ile Lys Asp Thr Glu Met Glu Pro Ser Leu
785                 790                 795                 800

Met Asp Gly Val Glu Tyr Gln Ala Gly Arg Phe Ala Leu Ser Leu Arg
                805                 810                 815

Gly Arg Cys Phe Ser Val Ile Leu Gly Ala Asn Thr Trp Pro Asp Leu
                820                 825                 830

Asp Leu Arg Asp Pro Val Cys Asp Asp Phe Phe Gln Leu Trp Gln Glu
                835                 840                 845

Thr Ala Glu Asn Asn Ala Thr Ile Tyr Glu Gln Ile Phe Arg Cys Leu
                850                 855                 860

Pro Ser Asn Ala Thr Arg Ser Leu Arg Leu Ser Gly Ser Met Trp Leu
865                 870                 875                 880

Trp Ser Pro Trp Leu Gln Ser Ala Phe Leu Ala Gln Ser Glu Leu Ala
                885                 890                 895

His Ile Gln Gly His Leu Val His Phe Pro Leu Lys Phe Leu Glu Asp
                900                 905                 910

Glu Ser Leu Leu Pro Pro Leu Gly Ser Lys Glu Gly Met Ile Pro Leu
            915                 920                 925

Glu Val Trp Thr
        930

(2) INFORMATION FOR SEQ ID NO:7:

(i) SEQUENCE CHARACTERISTICS:
        (A) LENGTH: 21 amino acids
        (B) TYPE: nucleic acid
```

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

TCCATCCAGG CCATTCTGCA CT                                                  22

(2) INFORMATION FOR SEQ ID NO:8:

(i) SEQUENCE CHARACTERISTICS:
         (A) LENGTH:  21 ami no acids
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CGTTGCTCTC AGCCATGTCT TG                                                  22
```

PHOSPHOLIPASE D POLYPEPTIDE AND DNA SEQUENCES

This application is a divisional of U.S. Application Ser. No. 08/968,752, filed Aug. 13, 1997, U.S. Pat. No. 6,043,073, issued Mar. 28, 2000, which claims priority from U.S. Provisional Application No. 60/025,469, filed Sep. 5, 1996.

TECHNICAL FIELD

This invention is in the field of molecular biology and particularly relates to nucleic acid sequences that encode novel phospholipases.

BACKGROUND

The mechanism by which specificity of physiological responses are conferred by a limited number of signal transducing substances, typically enzymes, is poorly understood. Cellular receptors on the surfaces of various cells are involved and initiate multiple signaling pathways. Some of the receptors on neutrophils are known: the PAF receptor, the interleukin-8 receptor and the fMetLeuPhe receptor all belong to the super-family of G-protein-linked receptors. A common feature of these receptors is that they span the cell membrane seven times, forming three extracellular and three intracellular loops and a cytoplasmic carboxy-terminal tail. The third loop and the tail exhibit extensive variability in length and sequence, leading to speculation that these parts are responsible for the selective interaction with the various G-proteins. Many of these G-protein-linked receptors stimulate the activation of three phospholipases, phospholipase C (PLC), phospholipase D (PLD) and phospholipase $A_2$ (PLA$_2$). These phospholipases constitute a family of regulatory enzymes which trigger various neutrophilic functions, for example adherence, aggregation, chemotaxis, exocytosis of secretory granules and activation of NADPH oxidase, i.e., the respiratory burst.

The main substrates for the phospholipases are membrane phospholipids. The primary substrates for PLC are the inositol containing lipids specifically and typically phosphotidylinositol (PI). PI is phosphorylated by PLC resulting in the formation of PIP, phosphotidylinositol 4-phosphate. The primary substrate for PLD and PLA$_2$ is phosphatidylcholine (PC), a relatively ubiquitous constituent of cell membranes. The activity of cytosolic PLA$_2$ on PC liberates arachidonic acid, a precursor for the biosynthesis of prostaglandins and leukotrienes and possible intracellular secondary messenger. PLD, on the other hand, catalyzes the hydrolytic cleavage of the terminal phosphate diester bond of glycerophospholipids at the P-O position. PLD activity was originally discovered in plants and only relatively recently discovered in mammalian tissues. PLD has been the focus of recent attention due to the discovery of its activation by fMetLeuPhe in neutrophils. PLD activity has been detected in membranes and in cytosol. Although a 30 kD (kilodalton) and an 80 kD activity have been detected, it has been suggested that these molecular masses represented a single enzyme with varying extents of aggregation. See Cockcroft, *Biochimica et Biophysica Acta* 1113: 135–160 (1992). One PLD has been isolated, cloned and partially characterized. See Hammond, *J. Biol. Chem.* 270:29640–43 (1995). Biological characterization of PLD1 revealed that it could be activated by a variety of G-protein regulators, specifically PKC (protein kinase C), ADP-ribosylation factor (ARF), RhoA, Rac1 and cdc-42, either individually or together in a synergistic manner, suggesting that a single PLD participates in regulated secretion in coordination with ARF and in propagating signal transduction responses through interaction with PKC, PhoA and Rac1. Nonetheless, PKC-independent PLD activation has been associated with Src and Ras oncogenic transformation, leaving open the possibility that additional PLDs might exist. See Jiang, *Mol. and Cell. Biol.* 14:3676 (1994) and Morris, *Trends in Pharmacological Sciences* 17: 182–85(1996). The difficulty may arise at least in part from the fact that in the phospholipase family enzymes may or may not be activated by, and catalyze, multiple substances, making sorting, tracking and identification by functional activities impractical.

There exists a need in the art for the identification and isolation of phospholipase enzymes. Without such identification and isolation, there is no practical way to develop assays for testing modulation of enzymatic activity. The availability of such assays provides a powerful tool for the discovery of modulators of phospholipase activity. Such modulators would be excellent candidates for therapeutics for the treatment of diseases and conditions involving pathological mitogenic activity or inflammation.

SUMMARY OF THE INVENTION

In one aspect, the invention provides novel mammalian phospholipase D (PLD) proteins, which are substantially free from other proteins with which they are typically found in their native state. These novel mammalian PLD proteins include polypeptides substantially free of association with other polypeptides and comprising an enzyme of mammalian origin having a phosphatidylcholine-specific pohspholipase D activity and containing at least two copies of the amino acid motif HXKXXXXD. More specifically, these proteins include polypeptides substantially free of association with other polypeptides and comprising PLD polypeptides that are perinuclear membrane associated, require PI(4,5)P2 for in vitro activity and are activated by one or more G-proteins. Alternatively, these proteins include polypeptides substantially free of association with other polypeptides and comprising PLD polypeptides that are plasma membrane associated, activate cytoskelatal reorganization pathways, require PI(4,5)P2 for in vitro activity and do not require Rac 1, cdc42, RhoA, PKC or ARF1 for activation.

These novel mammalian PLD proteins may be produced by recombinant genetic engineering techniques. They may also be purified from cell sources producing the enzymes naturally or upon induction with other factors. They may also be synthesized by chemical techniques, or a combination of the above-listed techniques. Mammalian PLD proteins from several species, termed PLD1a, PLD1b and PLD2, have been isolated. Human PLD1a and PLD1b are identical in amino acid sequence (SEQ ID NOS:2 and 5 respectively) except for a 38 amino acid segment that is missing from hPLD1b (SEQ ID NO:5), and present in hPLD1a (SEQ ID NO:2), beginning at amino acid number 585. Active mature PLD1a (SEQ ID NO:2) is an approximately 1074 amino acid protein, characterized by an apparent molecular weight for the mature protein of approximately 120 kD (kilodaltons) as determined by sodium dodecylsulfate polyacrylamide gel electrophoresis of protein purified from baculovirus expressing cells. The calculated molecular weight for the mature protein is approximately 124 kD. Active mature PLD1b (SEQ ID NO:5) is an approximately 1036 amino acid protein, characterized by an apparent molecular weight of approximately 120 kD as determined by sodium dodecylsulfate polyacrylamide gel electrophoresis of protein purified from baculovirus expressing cells. The calculated molecular weight for the mature protein is approximately 120 kD. Active mature PLD2 (SEQ ID NO:8) is an approximately 932 amino acid protein, characterized by an apparent molecular weight of approximately 112 kD as determined by sodium dodecylsulfate polyacrylamide gel electrophoresis of protein purified from baculovirus expressing cells. The calculated molecular weight for the mature protein is approximately 106 kD. As used herein, "PLD", "PLD1a", "PLD1b" or "PLD2" refer to any of the mammalian PLDs of this invention, "hPLD" refers to a human PLD of this invention and "mPLD" refers to a murine PLD of this invention.

Additionally, analogs of the PLD proteins and polypeptides of the invention are provided and include truncated polypeptides, e.g., mutants in which there are variations in the amino acid sequence that retain biological activity, as defined below, and preferably have a homology of at least 80%, more preferably 90%, and most preferably 95%, with the corresponding regions of the PLD1a, PLD1b or PLD2 amino acid sequences (SEQ ID NOS:2, 5 and 8 respectively). Examples include polypeptides with minor amino acid variations from the native amino acid sequences of PLD, more specifically PLD1a, PLD1b or PLD2 amino acid sequences (SEQ ID NOS:2, 5 and 8); in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on activity or functionality.

Using the PLD amino acid sequences of the invention (SEQ ID NOS:2, 5 and 8) other polypeptides or other DNA sequences encoding PLD proteins can be obtained. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. It also may be desirable to remove the region encoding the signal sequence, and/or to replace it with a heterologous sequence. It may also be desirable to ligate a portion of the PLD amino acid sequences (SEQ ID NOS:2, 5 and 8), particularly that which includes the amino terminal domain to a heterologous coding sequence, and thus to create a fusion peptide of PLD.

In designing such modifications, it is expected that changes to nonconserved regions of the PLD amino acid sequences (SEQ ID NOS:2, 5 and 8) will have relatively smaller effects on activity, whereas changes in the conserved regions, and particularly in or near the amino terminal domain are expected to produce larger effects. A residue which shows conservative variations among the PLD sequences and at least three of the other sequences is expected to be capable of similar conservative substitution of the PLD sequences. Similarly, a residue which varies nonconservatively among the PLD sequences and at least three of the other sequences is expected to be capable of either conservative or nonconservative substitution. When designing substitutions to the PLD sequences, replacement by an amino acid which is found in the comparable aligned position of one of the other sequences is especially preferred.

In another aspect, the invention provides compositions comprising a PLD1 or PLD2 of polypeptide in combination with at least one G-protein, for example ADP-ribosylation factor 1, RhoA, Rac1 or cdc42.

In another aspect, the invention provides novel, isolated, PLD DNA sequences not heretofore recognized or known in the art. The novel PLD DNA sequences encoding PLD1a and PLD1b proteins (SEQ ID NOS: 1 and 4) were isolated from a HeLa cell line and the novel PLD DNA sequence encoding mPLD2 protein (SEQ ID NO: 7) was isolated from a mouse embryonic cDNA library. As used herein, "isolated" means substantially free from other DNA sequences with which the subject DNA is typically found in its native, i.e., endogenous, state. These novel DNA sequences are characterized by comprising the same or substantially the same nucleotide sequence as in SEQ ID NOS:1, 3, 4, 5, 7 or 9, or active fragments thereof. The DNA sequences may include 5' and 3' non-coding sequences flanking the coding sequence. The 5' and 3' non-coding sequences for hPLD1a, hPLD1b and mPLD2 are illustrated in SEQ ID NOS: 3, 6 and 7 respectively. The nucleotide coding sequences only are illustrated in SEQ ID NOS: 1, 4 and 7 respectively. The DNA sequences of the invention also comprise nucleotide sequences capable of hybridizing under stringent conditions, or which would be capable of hybridizing under said conditions but for the degeneracy of the genetic code to a sequence corresponding to the sequence of SEQ ID NOS:1, 3, 4, 5, 7 or 8. SEQ ID NO:1 illustrates the DNA coding sequence of the novel PLD1a. The putative amino acid sequence of the PLD1a protein encoded by this PLD1a nucleotide sequence is illustrated in SEQ ID NO:2 and the DNA noncoding and coding sequences and putative amino acid sequence is illustrated in SEQ ID NO:3. SEQ ID NO:4 illustrates the DNA coding sequence of the novel PLD1b. The putative amino acid sequence of the PLD1b protein encoded by this PLD1b nucleotide sequence is illustrated in SEQ ID NO:5 and the DNA noncoding and coding sequences and putative amino acid sequence of PLD1b is illustrated in SEQ ID NO: 6. SEQ ID NO:7 illustrates the DNA sequence of the novel PLD2. The putative amino acid sequence of the PLD2 protein encoded by this PLD2 nucleotide sequence is illustrated in SEQ ID NO:8 and SEQ ID NO:9 illustrates the DNA noncoding and coding sequences and the putative amino acid sequence.

It is understood that the DNA sequences of this invention may exclude some or all of the signal and/or flanking sequences. In addition, the DNA sequences of the present invention may also comprise DNA capable of hybridizing under stringent conditions, or which would be capable of hybridizing under such conditions but for the degeneracy of the genetic code, to an isolated DNA sequence of SEQ ID NOS:1, 3, 4, 6, 7 or 9. As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 pg/ml salmon sperm DNA and 15% formamide at 68 degrees C.

Accordingly, the DNA sequences of this invention may contain modifications in the non-coding sequences, signal sequences or coding sequences, based on allelic variation, species or isolate variation or deliberate modification. Using the sequences of SEQ ID NOS:1, 3, 4, 6, 7 or 9, it is within the skill in the art to obtain other modified DNA sequences: the sequences can be truncated at their 3'-termini and/or their 5'-termini, the gene can be manipulated by varying individual nucleotides, while retaining the original amino acid (s), or varying the nucleotides, so as to modify amino acid(s). Nucleotides can be substituted, inserted or deleted by known techniques, including for example, in vitro mutagenesis and primer repair. In addition, short, highly degenerate oligonucleotides derived from regions of imperfect amino acid conservation can be used to identify new members of related families. RNA molecules transcribed from a DNA of the invention as described above, are an additional aspect of the invention.

Additionally provided by this invention is a recombinant DNA vector comprising vector DNA and a DNA sequence encoding a PLD polypeptide. The vector provides the PLD DNA in operative association with a regulatory sequence capable of directing the replication and expression of a PLD protein in a selected host cell. Host cells transformed with such vectors for use in expressing recombinant PLD proteins are also provided by this invention. Also provided is a novel process for producing recombinant PLD proteins or active fragments thereof. In this process, a host cell line transformed with a vector as described above containing a DNA sequence (SEQ ID NOS: 1, 3, 4, 6, 7 or 9) encoding expression of a PLD protein in operative association with a suitable regulatory sequence capable of directing replication and controlling expression of a PLD protein is cultured under appropriate conditions permitting expression of the recombinant DNA. The expressed protein is then harvested from the host cell or culture medium using suitable conventional means. This novel process may employ various known cells as host cell lines for expression of the protein. Currently preferred cells are mammalian cell lines, yeast, insect and bacterial cells. Especially preferred are insect cells and mammalian cell lines. Currently most especially preferred are baculovirus cells.

The practice of the invention will employ, unless otherwise indicated, conventional techniques of molecular biology, microbiology, recombinant DNA manipulation and production, and immunology, which are within the skill of the art. Such techniques are explained fully in the literature. See, e.g., Sambrook, *Molecular Cloning; A Laboratory Manual*, Second Edition (1989); *DNA Cloning*, Volumes I and II (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); *Transcription and Translation* (B. D. Hames and S. J. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice*, Second Edition (Springer-Verlag, N.Y.); and *Handbook of Experimental Immunology*, Volumes I–IV (D. M. Weir and C. C. Blackwell, Eds 1986). All patents, patent applications and publications mentioned herein, both supra and infra, are hereby incorporated by reference.

Another aspect of this invention provides pharmaceutical compositions for use in therapy, diagnosis, assay of PLD proteins, or in raising antibodies to PLD, comprising effective amounts of PLD proteins prepared according to the foregoing processes.

Yet another aspect of this invention provides a method to assess PLD modulation, useful in screening for specific PLD modulator molecules. By "PLD modulator molecule" we mean a substance that is capable of altering the catalytic activity or the cellular location of PLD1a, PLD1b or PLD2 under basal conditions or in the presence of regulatory molecules, for example, by changing the action of the PLD1, PLD1b or PLD2 enzyme or by changing the affinity of PLD1, PLD1b or PLD2 for its substrate. Such modulator molecules may comprise, without limitation, small molecule modulators or inhibitors of PLD catalytic activity such as small proteins, organic molecules or inorganic molecules. Such method comprises the steps of isolating and expressing a recombinant PLD protein of the invention (and/or their active domains) and employing such PLD protein in a solid-phase assay for PLD protein binding. Such solid phase assays are well know in the art. The availability of such assays, not heretofore available, permits the development of therapeutic modulator molecules, useful in the treatment of autoimmune or inflammatory diseases, such as for example rheumatoid arthritis, psoriasis and ulcerative colitis, in the treatment of wound healing and other diseases or conditions characterized by exhibition of an inflammatory response or in the treatment of cancer and other diseases characterized by pathogenic mitogenicity.

Further aspects of the invention therefore are pharmaceutical compositions containing a therapeutically effective amount of a PLD modulator molecule identified using the assays of the invention. Such PLD modulator molecule compositions may be employed in wound healing and in therapies for the treatment of autoimmune diseases or inflammatory diseases, for example rheumatoid arthritis, ulcerative colitis and psoriasis, and in the treatment of cancer and atherosclerosis, and other diseases characterized by exhibition of an inflammatory response or by pathogenic mitogenicity. These PLD modulator molecules may be presented in a pharmaceutically acceptable vehicle. These pharmaceutical compositions may be employed alone or in combination with other suitable pharmaceutical agents, in methods for treating the aforementioned disease states or conditions.

Such modulator molecule containing compositions may be used to inhibit neutrophil growth and differentiation, alone or in synergy with other treatment regimens such as chemotherapy and non-steroidal or steroidal anti-inflammatory drugs. A further aspect of the invention therefore is a method for treating these and/or other pathological states by administering to a patient a therapeutically effective amount of a PLD modulator in a suitable pharmaceutical carrier. These therapeutic methods may include administering simultaneously or sequentially with a PLD modulator an effective amount of at least one other phospholipase, cytokine, hematopoietin, interleukin, antibody, chemotherapeutic or anti-inflammatory.

Still another aspect of the invention are antibodies directed against PLD1a. PLD1b and/or PLD2 or a peptide thereof. Such antibodies may comprise PLD modulator molecules of the invention. As part of this aspect therefore, the invention claim cell lines capable of secreting such antibodies and methods for their production.

Additionally provided by this invention are compositions for detecting PLD dysfunction in mammals. These compositions comprise probes having at least one single-stranded fragment of at least 10 bases in length, more preferably 15 bases in length, of a novel PLD sequence, and fragments hybridizing to these single-stranded fragments under stringent hybridization conditions and non-cross-hybridizing with mammalian DNA. Such probe compositions may additionally comprise a label, attached to the fragment, to provide a detectable signal, as is taught in U.S. Pat. No. 4,762,780.

Further provided by this invention are methods for detecting a PLD condition in a human or other mammalian host. Such methods comprise combining under predetermined stringency conditions a clinical sample suspected of containing PLD DNA with at least one single-stranded DNA fragment of the novel PLD sequences having at least 10 bases, more preferably 15 bases, and being non-cross-hybridizing with mammalian DNA, and detecting duplex formation between the single-stranded PLD fragments and the sample DNA. Alternatively, PCR may be used to increase the nucleic acid copy number by amplification to facilitate the identification of PLD in individuals. In such case, the single-stranded PLD DNA sequence fragments of the present invention can be used to construct PCR primers for PCR-1 based amplification systems for the diagnosis of PLD conditions. Such systems are well known in the art. See for example, U.S. Pat. No. 5,008,182 (detection of AIDS associated virus by PCR) and Hedrum, PCR *Methods and Applications* 2:167–71(1992) (detection of Chlamydia trachomatis by PCR and immunomagnetic recovery).

Other aspects and advantages of this invention are described in the following detailed description.

DETAILED DESCRIPTION

A. Introduction

The present invention provides biologically active mammalian phospholipases, (mammalian PLDs), in forms substantially free from association with other mammalian proteins and proteinaceous material with which they are typically found in their native state. These proteins can be produced by recombinant techniques to enable large quantity production of pure, active mammalian PLDs useful for therapeutic applications. Alternatively, these proteins may be obtained as homogeneous proteins purified from a mammalian cell line secreting or expressing it. Further mammalian PLDs, or active fragments thereof, may be chemically synthesized.

B. Identification of PLD DNA Sequences, Protein Characterization

Three members of the mammalian PLD family are disclosed: PLD1a was initially identified as a by product of a screening assay that had uncovered a yeast PC-specific PLD gene. See Rose, *Proc. Natl. Acad. Sci.* 92:12151–55 (1995). The yeast PLD gene identified a GenBank human-expressed sequence tag (EST) encoding a significantly similar peptide sequence. Primers were developed and HeLa cDNA was amplified by PCR (polymerase chain reaction) using oligonucleotide primers matching the EST. Amplification of the EST using the primers yielded a PCR product which was then used as a hybridization probe to screen a publicly available HeLa cDNA library at high stringency. Analysis of positive clones revealed a cDNA encoding what appeared to be a novel PLD enzyme. SEQ ID NO:1 illustrates the cDNA coding sequence of this clone, called PLD1a. SEQ ID NO:3 illustrates the 5' and 3' noncoding regions and the cDNA coding sequence. The nucleotide sequence (SEQ ID NO:3) comprises 3609 base pairs, including a 5' noncoding sequence of 95 base pairs, a 3' noncoding sequence of 292 base pairs and a coding sequence of 3222 base pairs. The PLD1a sequence is characterized by a single long open reading frame encoding a 1074 amino acid sequence beginning with the initiation methionine at nucleotide position 96. SEQ ID NO:2 illustrated the predicted amino acid sequence of the PLD1a polypeptide.

PLD1b was initially isolated during examination of human PLD1a mRNA regulation in HL-60 cells. A reverse transcription polymerase chain reaction assay (RT-PCR) was employed using primers based on the PLD1a reported sequence that would amplify a central fragment of the coding region. See Hammond, *J. Biol. Chem.* 270:29640–43 (1995). In addition to a PCR product of the expected size for hPLD1a, an additional and smaller fragment was amplified as well. Both fragments were cloned and sequenced. The larger band corresponded to the expected amplification product, hPLD1a (SEQ ID NO:1), and the shorter product corresponded to an altered form, hPLD1b (SEQ ID NO:4), from which 114 nucleotides (38 amino acids) were missing.

Using degenerate primers corresponding to the sequences encoded by the PLD1a based central region primers to amplify PLD1 from rat PC12 cells and mouse embryonic cells, analogous results were obtained, demonstrating that the splice variant PLD1b (SEQ ID NOS:4 and 6) most likely represents an alternative splicing event of biological significance, because it is conserved in both murine and human cells. Tissue analysis shows that the "b" form predominates in mouse embryos, brain, placenta and muscle, although the "a" form is additional present in each case.

Human PLD1b was sequenced. SEQ ID NO:4 illustrates the cDNA coding sequence. SEQ ID NO:5 illustrates the putative amino acid sequence (single letter code). SEQ ID NO:6 illustrates the cDNA sequence, including non-coding and coding regions, and the putative amino acid sequence (single letter code).

The nucleotide sequence of PLD1b comprises 3495 base pairs, including a 5' noncoding sequence of 95 base pairs. The sequence also shows a 3' noncoding sequence of 292 base pairs. Thus, the nucleotide sequence contains a single long reading frame of 3108 nucleotides.

The mammalian PLD1b sequence is characterized by a single long open reading frame predicting an unprocessed 1036 amino acid polypeptide beginning at nucleotide position 96 of SEQ ID NO:6. PLD1 and PLD2 appear structurally dissimilar to other proteins, except other PLD proteins, with which they share similar structural features and domains. See Morris, *Trends in Pharmacological Science* 17:182–85(1996).

Mammalian PLD2 was initially isolated from a publicly available mouse embryonic cDNA library (Stratagene) using the full length PLD1a sequence (SEQ ID NO: 1) as a probe to screen the library using conditions of low stringency as described in Maniatis, *Molecular Cloning (A Laboratory Manual)*, Cold Spring Harbor Laboratory (1982). Murine PLD2 was sequenced. SEQ ID NO:7 illustrates the cDNA coding sequence. SEQ ID NO:8 illustrates the putative amino acid sequence (single letter code). SEQ ID NO:9 illustrates the cDNA sequence, including non-coding and coding regions, and the putative amino acid sequence (single letter code).

The nucleotide sequence of PLD2 comprises 3490 base pairs, including a 5' noncoding sequence of 138 base pairs. The sequence also shows a 3' noncoding sequence of 556 base pairs. Thus, the nucleotide sequence contains a single long reading frame of 2796 nucleotides.

The mammalian PLD2 sequence is characterized by a single long open reading frame predicting an unprocessed 932 amino acid polypeptide beginning at nucleotide position 139 of SEQ ID NO:9.

The nucleotide sequences of hPLD1a (SEQ ID NO:1), hPLD1b (SEQ ID NO:4) and mPLD2 (SEQ ID NO:7) have been compared with the nucleotide sequences recorded in GenBank. Other than homology with each other and other PLD proteins, no significant similarities in nucleotide sequence were found with the published DNA sequences of other proteins. No significant homology was found between the coding sequences of hPLD1a hPLD1b or mPLD2 (SEQ ID NOS:2, 5 AND 8) and any other published non-PLD polypeptide sequence.

Preliminary biological characterization indicates that mammalian PLD1 (SEQ ID NOS:2 or 5) is primarily associated with Golgi and other perinuclear membrane structures and is involved in the regulation of intravesicular membrane trafficking. PLD1 is activated by Rac1, cdc42, RhoA, PKC and ARF1, and requires $PI(4,5)P_2$ for activity in vitro. Like PLD1, PLD2 requires $PI(4,5)P_2$ for in vitro activity, but PLD2 primarily is associated with the plasma membrane; its overexpression results in a phenotypic change in cell morphology. Cells expressing PLD2 exhibit increases in lamellapodia formation similar in some respects to overexpression phenotypes generated using activated cdc42, Rac1, RhoA or membrane-targeted Ras, suggesting that PLD2 activates similar cytoskeletal reorganization pathways either in parallel or in series with one or more of these other activators. In further contrast to PLD1, PLD2 does not require Rac1, cdc42, RhoA, PLC or ARF1 for activation and PLD2 is down-regulated by a specific cytosolic brain inhibitor that does not inhibit PLD1 or PLC.

The PLD polypeptides provided herein also include polypeptides encoded by sequences similar to that of PLD1a, PLD1b and PLD2 (SEQ ID NOS:2, 5 and 8 respectively), but into which modifications are naturally provided or deliberately engineered. This invention also encompasses such novel DNA sequences, which code for expression of PLD polypeptides having phosphatidyl choline-specific PLD activity. These DNA sequences include sequences substantially the same as the DNA sequences (SEQ ID NO: 1, 3, 4, 6, 7 and 9) and biologically active fragments thereof, and such sequences that hybridize under stringent hybridization conditions to the DNA sequences (SEQ ID NOS: 1, 3, 4, 6, 7 and 9). See Maniatis, *Molecular Cloning (A Laboratory Manual)*, Cold Spring Harbor Laboratory (1982), pages 387–389. One example of such stringent conditions is hybridization at 4×SSC, at 65 C., followed by a washing in 0.1×SSC at 65 C. for one hour. Another exemplary stringent hybridization scheme uses 50% foramide, 4×SSC at 42 C.

DNA sequences that code for PLD polypeptides but differ in codon sequence due to the degeneracies inherent in the genetic code are also encompassed by this invention. Allelic variations, i.e., naturally occurring interspecies base changes that may or may not result in amino acid changes, in the PLD DNA sequences (SEQ ID NOS: 1, 3, 4, 6, 7 and 9) encoding PLD polypeptides (SEQ ID NOS: 2, 5 and 8) having phosphatidyl choline-specific PLD activity are also included in this invention.

Methods for producing a desired mature polypeptide can include the following techniques. First, a vector coding for a PLD polypeptide can be inserted into a host cell, and the host cell can be cultured under suitable culture conditions permitting production of the polypeptide.

The PLD DNA sequences or active fragments thereof can be expressed in a mammalian, insect, or microorganism host. The PLD polynucleotides are inserted into a suitable expression vector compatible with the type of host cell employed and operably linked to the control elements within that vector. Vector construction employs techniques that are known in the art. Site-specific DNA cleavage involved in such construction is performed by treating the vector with suitable restriction enzymes under conditions which generally are specified by the manufacturer of these commercially available enzymes. A suitable expression vector is one that is compatible with the desired function (e.g. transient expression, long term expression, integration, replication, amplification) and in which the control elements are compatible with the host cell.

In order to obtain PLD expression, recombinant host cells derived from transformants are incubated under conditions which allow expression of the PLD encoding sequence (SEQ ID NOS: 1, 3, 4, 6, 7 and 9). These conditions will vary, depending upon the host cell elected. However, the conditions are readily ascertainable to those of ordinary skill in the art, based upon what is known in the art. Detection of a PLD protein expressed in the transformed host cell can be accomplished by several methods. For example, detection can be by enzymatic activity (or increased enzymatic activity or increased longevity of enzymatic activity) using fluorogenic substrates which are comprised of a dibasic cleavage site for which an PLD protein is specific. A PLD protein can also be detected by its immunological reactivity with anti-PLD antibodies.

C. PLD Modulator Molecules

A method is provided for identifying molecules which modulate the catalytic activity of PLD by causing a detectable loss in that activity. The method comprises transfecting a cell line with an expression vector comprising nucleic acid sequences encoding a PLD sequence or active domain or fragment thereof and expressing a PLD protein. The modulator molecule is identified by adding an effective amount of an organic compound to the culture medium used to propagate the cells expressing the PLD protein or active domain or fragment thereof. An effective amount is a concentration sufficient to block the catalysis of phosphatidylcholine and the formation of phosphatidic acid and choline. The loss in catalytic activity may be assayed using various techniques, using intact cells or in solid-phase assays.

For example, binding assays similar to those described for IL-7 in U.S. Pat. No. 5,194,375 may be used. This type of assay would involve labeling PLD and quantifying the amount of label bound by PLD ligand in the presence and absence of the compound being tested. The label used may, for example, be a radiolabel, e.g., 1251 or a fluorogenic label.

Alternatively, an immunoassay may be employed to detect PLD catalytic activity by detecting the immunological reactivity of PLD with anti-PLD antibodies in the presence and absence of the compound being tested. The immunoassay may, for example, involve an antibody sandwich assay or an enzyme-linked immunoassay. Such methods are well known in the art and are described in *Methods in Enzymology*, Vols. 154 and 155 (Wu and Grossman, and Wu, Eds., respectively), (Mayer and Walker, Eds.) (1987); *Immunochemical Methods in Cell and Molecular Biology* (Academic Press, London).

One assay which could be employed is disclosed in detail Example 3. In such as assay the potential modulator molecule to be tested may be added to the initial mixture or after addition of the labeled lipid mixture.

Pharmaceutical compositions comprising the PLD modulator molecule may be used for the treatment of autoimmune diseases such as rheumatoid arthritis, psoriasis and ulcerative colitis, inflammatory diseases, wound healing and other diseases or conditions characterized by exhibition of an inflammatory response, or in the treatment of cancer and other diseases characterized by pathogenic mitogenicity. Such pharmaceutical compositions comprise a therapeutically effective amount of one or more of the modulators in admixture with a pharmaceutically acceptable carrier. Other adjuvants, for instance, MF59 (Chiron Corp.), QS-21 (Cambridge Biotech Corp.), 3-DMPL (3-Deacyl-Monophosphoryl Lipid A) (RibiImmunoChem Research, Inc.), clinical grade incomplete Freund's adjuvant (IFA), fusogenic liposomes or water soluble polymers may also be used. Other exemplary pharmaceutically acceptable carriers or solutions are aluminum hydroxide, saline and phosphate buffered saline. Such pharmaceutical compositions may also contain pharmaceutically acceptable carriers, diluents, fillers, salts, buffers, stabilizers and/or other materials well known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

Administration can be carried out in a variety of conventional ways. The composition can be systemically administered, preferably subcutaneously or intramuscularly, in the form of an acceptable subcutaneous or intramuscular solution. The preparation of such solutions, having due regard to pH, isotonicity, stability and the like is within the skill in the art. In the long term, however, oral administration will be advantageous, since it is expected that the active modulator compositions will be used over a long time period to treat chronic conditions. The dosage regimen will be determined by the attending physician considering various factors known to modify the action of drugs such as for example, physical condition, body weight, sex, diet, severity of the condition, time of administration, activity of the modulator and other clinical factors. It is currently contemplated, however, that the various pharmaceutical compositions should contain about 10 micrograms to about 1 milligram per milliliter of modulator.

In practicing the method of treatment of this invention, a therapeutically effective amount of the pharmaceutical composition is administered to a human patient in need of such treatment. The term "therapeutically effective amount" means the total amount of the active component of the method or composition that is sufficient to show a meaningful patient benefit. i.e., healing of the condition or increase in rate of healing. A therapeutically effective dose of a modulator composition of this invention is contemplated to be in the range of about 10 micrograms to about 1 milligram per milliliter per dose administered. The number of doses administered may vary, depending on the individual patient and the severity of the condition.

D. Diagnostic Assays and Use as a Marker

The novel DNA sequences of the present invention can be used in diagnostic assays to detect PLD1 and/or PLD2 activity in a sample, using either chemically synthesized or recombinant DNA fragments. In yet another embodiment, fragments of the DNA sequences can also be linked to secondary nucleic acids with sequences that either bind a solid support or other detection probes for use in diagnostic assays. In one aspect of the invention, fragments of the novel DNA sequences (SEQ ID NOS:1,4 and 7) comprising at least between 10 and 20 nucleotides can be used as primers to amplify nucleic acids using PCR methods well known in the art and as probes in nucleic acid hybridization assays to detect target genetic material such as PLD DNA in clinical specimens (with or without PCR). See for example, U.S. Pat. Nos. 4,683,202; 4,683,195; 5,091,310; 5,008,182 and 5,168,039. In an exemplary assay, a conserved region of the novel DNA sequence is selected as the sequence to be amplified and detected in the diagnostic assay. Oligonucleotide primers at least substantially complementary to (but preferably identical with) the sequence to be amplified are constructed and a sample suspected of containing a PLD nucleic acid sequence to be detected is treated with primers for each strand of PLD nucleic acid sequence to be detected, four different deoxynucleotide triphosphates and a polymerization agent under appropriate hybridization conditions such that an extension product of each primer is synthesized that is complementary to the PLD nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the novel DNA sequence, capable of hybridizing with the amplified sequence as is well known in the art. See, e.g. U.S. Pat. No. 5,008,182.

In another embodiment the probes or primers can be used in a marker assay to detect defects in PLD1 and/or PLD2 function. Introduction of a restriction site into the novel DNA sequence will provide a marker that can be used with PCR fragments to detect such differences in a restriction digest. Such procedures and techniques for detecting sequence variants, such as, point mutations with the expected location or configuration of the mutation, are known in the art and have been applied in the detection of sickle cell anemia, hemoglobin C disease, diabetes and other diseases and conditions as disclosed in U.S. Pat. No. 5,137,806. These methods are readily applied by one skilled in the art to detect and differentiate between sequence variants of PLD1 and/or PLD2.

In another embodiment the novel DNA sequences can be used in their entirety or as fragments to detect the presence of DNA sequences, related sequences, or transcription products in cells, tissues, samples and the like using hybridization probe techniques known in the art or in conjunction with one of the methods discussed herein. When used as a hybridization probe, fragments of the novel DNA sequences of the invention are preferably 50–200 nucleotides long, more preferably 100–300 nucleotides long and most preferably greater than 300 nucleotides long.

E. Vectors

The novel DNA sequences of the invention can be expressed in different vectors using different techniques known in the art. The vectors can be either single stranded or double stranded and made of either DNA or RNA. Generally, the DNA sequence is inserted into the vector alone or linked to other PLD genomic DNA. In direct in vitro ligation applications, the isolated sequence alone is used. The sequence (or a fragment thereof) in a vector is operatively linked to at least a promoter and optionally an enhancer.

F. Novel Proteins

The DNA sequences, analogs or fragments thereof can be expressed in a mammalian, insect, or microorganism host. The polynucleotide is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors suitable for replication in mammalian cells are known in the art. Such suitable mammalian expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis,*Science* 236:1237(1987), Alberts, *Molecular Biology of the Cell,* 2nd Ed. (1989). Enhancers derived from viruses may be particularly useful, because they typically have a broader host range. Examples include the SV40 early gene enhancer (see Dijkema, *EMBO J.* 4:761(1985)) and the enhancer/promoters derived from the long terminal repeat (LTR) of the RSV (see Gorman, *Proc. Natl. Acad. Sci.* 79: 6777(1982b)) and from human cytomegalovirus (see Boshart, *Cell* 41: 521(1985)). Additionally, some enhancers are regulatable and become active only in the presence of an inducer, such as a hormone or metal ion (see Sassone-Corsi and Borelli, *Trends Genet.* 2: 215(1986)); Maniatis, *Science* 236: 1237(1987)). In addition, the expression vector can and will typically also include a termination sequence and poly(A) addition sequences which are operably linked to the PLD coding sequence.

Sequences that cause amplification of the gene may also be desirably included in the expression vector or in another vector that is co-translated with the expression vector containing a PLD DNA sequence, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes a novel PLD protein or polypeptide of this invention can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into mammalian cells are known in the art and include dextran-mediated transfection, calcium phosphate precipitation, polybrene mediated transfection, protoplast fusion, electroporation, encapsulation of the polynucleotide (s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, *Virology* 17: 31(1989).

The plasmid can also contains the polyhedron polyadenylation signal and a procaryotic ampicillin-resistance (amp) gene and origin of replication for selection and propagation in *E. coli*. See Miller, *Ann. Rev. Microbiol.* 42: 177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

A preferred baculovirus expression system employs Sf9 cells, as detailed in Example 3.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3) transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EP Patent Pub. No. 329 203). The yeast PHO5 gene, encoding acid phosphatase, also provides useful promoter sequences. See Myanohara, *Proc. Natl. Acad. Sci.* 80: 1(1983).

A PLD DNA sequence, analog or an active fragment thereof can be expressed intracellularly in yeast. A promoter sequence can be directly linked with the sequence or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of a sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of a sequence and expressed in yeast. The DNA sequence at the junction of the two amino acid sequences may or may not encode a clearable site. See, e.g., EP Patent Pub. No. 196 056. Alternatively, the polypeptides can also be secreted from the cell into the growth media by creating a fusion protein comprised of a leader sequence fragment that provides for secretion in yeast or bacteria of the polypeptides. Preferably, there are processing sites encoded between the leader fragment and the sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the polypeptide encoded by the DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8: 17–24 (1979)), pC1/1 (see Brake. *Proc. Natl. Acad. Sci.* 81: 4642–4646(1984)), and YRp17 (see Stinchcomb, *J. Mol. Biol.* 158: 157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101: 228–245(1983) and Rine, *Proc. Natl. Acad. Sci.* 80: 6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol.Cell.Biol.* 6: 142(1986), *Candida maltosa* (Kunze, *J. Basic Microbiol.* 25: 141(1985), *Hansenula polymorpha* (Gleeson, *J. Gen. Microbiol.* 132: 3459(1986) and Roggenkamp, *Mol. Gen. Genet.* 202: 302(1986), *Kluyveromyces fragilis* (Das, *J. Bacteriol.* 158: 1165(1984), *Kluyveromyces lactis* (De Louvencourt, *J. Bacteriol.* 154: 737(1983) and Van den Berg, *Bio/Technology* 8: 135(1990), *Pichia guillerimondii* (Kunze, *J. Basic Microbiol.* 25: 141 (1985), *Pichia pastoris* (Cregg, *Mol. Cell. Biol.* 5: 3376 (1985), *Saccharomyces cerevisiae* (Hinnen, *Proc. Natl. Acad. Sci.* 75: 1929(1978) and Ito, J. Bacteriol. 153: 163 (1983), *Schizosaccharomyces pombe* (Beach and Nurse, *Nature* 300: 706(1981), and *Yarrowia lipolytica* (Davidow, *Curr. Genet.* 10: 380471(1985) and Gaillardin, *Curr. Genet.* 10: 49(1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18: 173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (see Chang, *Nature* 198: 1056(1977), and maltose. Additional examples include promoter sequences derived from biosynthetic enzymes such as tryptophan (trp) (see Goeddel, *Nuc. Acids Res.* 8: 4057(1981), Yelverton, *Nuc. Acids Res.* 9: 731(1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid, promoter such as the tac promoter (see U.S. Pat. No. 4,551,433, Amann, *Gene* 25: 167(1983) and de Boer, *Proc. Natl. Acad. Sci.* 80: 21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189: 113(1986) and Tabor, *Proc. Natl. Acad. Sci.* 82: 1074(1985)).

In addition to a functioning promoter sequence, an efficient ribosome binding site is also useful for the expression of the DNA sequence or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254: 34(1975). The SD sequence is thought to promote binding of mRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

The novel PLD proteins of the invention can be expressed intracellularly. A promoter sequence can be directly linked with a novel PLD DNA sequence, analog or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of an sequence fragment thereof and expressed in bacteria. The resulting fusion protein preferably retains a site for a processing enzyme (factor Xa) to cleave the bacteriophage protein from the sequence or fragment thereof (see Nagai, *Nature* 309: 810(1984). Fusion proteins can also be made with sequences from the lacZ gene (Jia, *Gene* 60: 197(1987),the trpE gene (Allen, *J. Biotechnol.* 5: 93(1987) and Makoff, *J. Gen. Microbiol.* 135: 11(1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the polypeptide. Through this method, mature PLD1b and/or PLD2 polypeptides can be isolated. See Miller, *Bio/Technology* 7: 698 (1989).

Alternatively, proteins or polypeptides can also be secreted from the cell by creating chimeric DNA molecules that encode a fusion protein comprised of a signal peptide sequence fragment that provides for secretion of the proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the protein or polypeptide.

DNA encoding suitable signal sequences can be derived from genes for secreted bacterial proteins, such as the *E. coli* outer membrane protein gene (ompA) (Masui, *Experimental Manipulation of Gene Expression* (1983) and Ghrayeb, *EMBO J.* 3:2437 (1984)) and the *E. coli* alkaline phosphatase signal sequence (phoA) (see Oka, *Proc. Natl. Acad. Sci.* 82: 7212 (1985). The signal sequence of the alpha-amylase gene from various Bacillus strains can be used to secrete heterologous proteins from *B. subtilis* (see Palva, *Proc. Natl. Acad. Sci.* 79: 5582 (1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the PLD1b and/or PLD2 protein or polypeptide encoded by the DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, *Ann. Rev. Microbiol.* 32: 469 (1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosomal vector or an integrating vector, as described above.

Expression and transformation vectors, either extrachromosomal or integrating, have been developed for transformation into many bacteria. Exemplary are the expression vectors disclosed in Palva, *Proc. Natl. Acad. Sci.* 79: 5582 (1982), EP Patent Pub. Nos. 036 259 and 063 953 and PCT Patent Publication WO 84/04541 (for *B.subtilis*); in Shimatake, *Nature* 292: 128 (1981), Amann, *Gene* 40: 183 (1985), Studier, *J. Mol. Biol.* 189: 113 (1986) and EP Patent Pub. Nos. 036 776, 136 829 and 136 907 (for *E. coli*); in Powell, *Appl. Environ. Microbiol.* 54: 655 (1988) and U.S. Pat. No. 4,745,056 (for Streptococcus).

Methods of introducing exogenous DNA into bacterial hosts are well-known in the art, and typically include either the transformation of bacteria treated with CaCl2 or other agents, such as divalent cations and DMSO. DNA can also be introduced into bacterial cells by electroporation. Exemplary methodologies can be found in Masson, *FEMS Microbiol. Let.* 60: 273 (1989), Palva, *Proc. Natl. Acad. Sci.* 79: 5582 (1982), EP Patent Pub. Nos. 036 259 and 063 953 and PCT Patent Pub. WO 84/04541 for Bacillus transformation. For campylobacter transformation, see e.g., Miller, *Proc. Natl. Acad. Sci.* 85: 856 (1988) and Wang,. *J. Bacteriol.*172: 949 (1990). For *E. coli*, see e.g., Cohen, *Proc. Natl. Acad. Sci.* 69: 2110 (1973), Dower, *Nuc. Acids Res.* 16: 6127 (1988), Kushner, *Genetic Engineering: Proceedings of the International Symposium on Genetic Engineering* (eds. H. W. Boyer and S. Nicosia), Mandel, *J. Mol. Biol.* 53: 159 (1970) and Taketo, *Biochem. Biophys. Acta* 949: 318 (1988). For Lactobacillus and Pseudomonas, see e.g., Chassy, *FEMS Microbiol. Let.* 44: 173 (1987) and Fiedler, *Anal. Biochem.* 170: 38 (1988), respectively. For Streptococcus, see e.g., Augustin, *FEMS Microbiol. Let.* 66: 203 (1990), Barany, *J. Bacteriol.* 144: 698 (1980), Harlander, *Streptococcal Genetics* (ed. J. Ferretti and R. Curtiss III)(1987), Perry, *Infec. Immun.* 32: 1295 (1981), Powell, *Appl. Environ. Microbiol.* 54: 655 (1988) and Somkuti, *Proc. 4th Evr. Cong. Biotechnology* 1: 412 (1987).

The present invention is illustrated by the following examples.

Materials and Methods

Polymerase Chain Reactions (PCR)

PCRs were carried out as follows. HeLa cells were obtained from the American Type Culture Collection (ATCC). The cells were grown in DMEM supplemented with fetal calf serum. Total RNA was isolated from the HeLa cells by the method of Chomczynski and Sacchi. See Chomczynski, *Anal. Biochem.* 162: 156–59 (1987). Poly A+ RNA was obtained by affinity chromatography on oligo dT cellulose columns (Pharmacia, Piscataway, N.J.). First strand cDNA synthesis was performed starting with 5 g of HeLa poly A+ RNA according to the manufacturer's instructions (Pharmacia).

PCR reactions were carried out for 30 cycles beginning with a 1-minute incubation at 94 C., 2 minutes at 50 C., 1.5 minutes at 72 C., and a final elongation step at 72 C. for 4 minutes using the PCR primers described below at a final concentration of 0.25 M and HeLa cDNA at approximately 10 ng/ml. PCR products migrating between 200 and 400 base pairs on a 1.5% agarose gel were excised, subcloned into Bluescript (sk) and manually sequenced as described by Sanger, *Proc. Natl. Acad. Sci.* 74: 5463–67 (1977). In some instances, annealing temperatures, extensions and the number of cycles were adjusted to optimize amplification. Sequence analysis revealed cDNAs encoding the predicted fragments upon which the primers were designed. To obtain a full-length version of this clone, a bacteriophage lambda cDNA library was screened.

Nucleotide Sequence Determination and Analysis

All nucleic acid sequences were determined by the dideoxynucleotide chain termination method (Sanger et al., 1977). A variety of templates were prepared for sequencing; they included double-stranded plasmid DNA and PCR products. Manual sequencing was employed. The sequence was determined for both strands. Ambiguous regions were corrected by additional sequencing after proofreading. The primers used for sequencing were synthesized on a Model 1000 Beckman Instruments DNA synthesizer. The contig and analysis of the sequence were performed using MacD-NASIS (Hitachi). The homology searches were performed using the BLAST program through NCBI services.

EXAMPLE 1

Identification and Isolation of PLD-1a cDNAs encoding PC-specific activity were identified during a screen that uncovered the yeast PC-specific PLD gene SP014, as described in Rose, *Proc. Natl. Acad. Sci.* 92: 12151–55 (1995). Homology analysis of the yeast PLD identified a GenBank human expressed sequence tag (EST) encoding a significantly similar peptide sequence. A hybridization probe was generated from random-primed HeLa cDNA using PCR and primers specific to the EST and used to screen a Zap II HeLa cDNA library (Stratagene). Nine hybridizing clones were detected. Sequence analysis of the hybridizing clones (using Sequenase version 2.0, U.S. Biochemical Corp.) revealed a large open reading frame encoding a 1074 amino acid protein. SEQ ID NOS: 1 and 2 illustrate the cDNA coding sequence and predicted amino acid sequence (single letter code) of the human clones of the PLD1a polypeptide. SEQ ID NO:3 illustrates the cDNA sequence including 5' and 3' noncoding regions along with the predicted amino acid sequence. The predicted amino acid sequence is also published in Hammond, *J. Biol. Chem.* 270: 29640–43 (1995). The initiator methionine conforms to the eukaryotic consensus sequence and is the first in-frame methionine in the 5' untranslated region. An in-frame stop codon is located at nucleotides 16–17 of the cDNA, indicating that the coding region is full length. The entire 3' untranslated region was probably not obtained because a recognizable polyadenylation signal sequence is not present at the 3' end.

Human PLD1a is devoid of heretofore recognized domain structures, in contrast to the various isoforms of PLC which contain SH2, SH3 or PH domains. In addition, no similarity exists between human PLD1 and PLC or phosphatidylinositol-glycan-specific PLD. See Scallon, *Science* 252:445–448 (1991). Human PLD1a bears no similarity to proteins known to bind $PIP_2$ or $IP_3$, such as PLC-, $PI_3$-kinase, or the $IP_3$ receptor.

Data base searching using human PLD1a identified homologs in numerous widely disparate organisms, demonstrating that PLD1a is a member of a novel but highly conserved gene family. Only one of these cDNAs was recognized to encode a PC-PLD enzyme (castor bean); the remainder constitutes ESTs or hypothetical open reading frames. A comparison of the related sequences reveals the location of several blocks of highly conserved amino acids, one or more of which might constitute critical portions of the catalytic or cofactor binding sites. Two regions in particular, amino acids 455 through 490 and 892 through 926, are highly conserved in all of the PLD1-related genes and contain an invariant charged motif, HXKXXXXD. Mammalian PLD is believed to be intracellular and membrane-associated, as opposed to being an integral membrane protein. Consistent with this speculation, the human PLD1a provided herein encodes neither a signal peptide nor a hydrophobic transmembrane sequence.

EXAMPLE 2

Identification and Isolation of the hPLD1b Splice Variant

To examine hPLD1a mRNA regulation in HL-60 cells a RT-PCR assay using primers that would amplify a central fragment of the coding region was conducted. HL-60 cells, maintained in RPMI-1640 medium supplemented with 10% fetal bovine serum, 100 units/ml penicillin and 100 g/ml streptomycin in a humidified atmosphere containing 5% $CO_2$, at 37 C., were grown in RPMI-1640 medium without fetal bovine serum for 24 hours. Total RNA was isolated from the HL-60 cells by the acid guanidine thiocyanate method following the method of Chomczynski, *Anal. Biochem.* 162:156–62 (1992). Two g of RNA was reverse transcribed by using random hexamer mixed primers. The number of amplification cycles were determined to individual primer sets in order to maintain exponential rate of product amplification. Amplified DNA fragments were subjected to electrophoresis on 1.5% agarose gel and visualized by ethidium bromide staining. Primer A (Forward): nucleotides 1475 through 1491; primer B (reverse) nucleotides 2133 through 2113 of SEQ ID NO: 1. Amplification conditions used were 94 C. for 30 seconds, 60 C. for 1 minute, and 72 C. for 1 minute; 25–27 cycles.

A PCR product of the expected size (633 nucleotides) was generated, demonstrating that hPLD1a is expressed in HL-60 cells. In addition, an additional smaller fragment was amplified. Both fragments were cloned and sequenced employing the above-described methods. The larger band corresponded to the expected amplification product, hPLD1a. The shorter product corresponded to an altered form from which 114 nucleotides (38 amino acids) were missing. Amplification with appropriately chosen junction primers permitted amplification of each product independently. The cDNA coding sequence for this splice variant is illustrated in SEQ ID NO:4. The putative amino acid sequence is illustrated in SEQ ID NO:5. The cDNA sequence, including 5' and 3' noncoding regions, along with the putative amino acid sequence is illustrated in SEQ ID NO:6. Examination of genomic sequence at the position of amino acid 623, the 3' junction of the missing sequence, revealed that an acceptable splice donor site, an 11 nucleotide T/C rich sequence followed by any nucleotide and AGAT, was present and that the adjacent genomic sequence does not encode the nucleotide sequence found in either the short or the long form. Thus, the long form, hPLD1a, encodes an alternately spliced exon not present in the short form, hPLD1b, and does not represent a partially processed mRNA. Subsequent analysis of five of the original cDNAs obtained from the HeLa cell cDNA library screened in Example 1 revealed that two of the cDNAs encoded the long form and three of the cDNAs encoded the short form.

Degenerate primers corresponding to the sequences encoded by primers A and B were used to amplify PLD1 from rat PC12 cells. Analogous results were obtained, demonstrating that the alternate splicing event most likely has biological significance, since it is conserved in both rat and human. The short form was also detected in mouse tissue and predominated in embryos, brain, placenta and muscle, although the long form is also present in each case.

The exon is located in a "loop" region of hPLD1a which is present in the center of the mammalian PLD1 protein but which is absent from plant, yeast, all lower organisms, and mammalian PLD2 (see Example below). Amplification of the same region of mPLD2 was carried out; no alternative splicing was observed.

EXAMPLE 3

Expression in Mammalian Cells and in Baculovirus

To investigate their catalytic properties and activation requirements, hPLD1a and hPLD1b were expressed in Sf9 insect cells using baculovirus, and in COS-7 cells.

For baculovirus expression, the hPLD1a cDNA was inserted into the unique SmaI and NotI sites of the PVL1392 transfer vector (Invitrogen, Inc.) and recombinant baculoviruses harboring the cDNA were generated, selected and propagated using standard methods as described in Lucklow, *Bio/Technology* 6:47–55 (1988). Monolayers of Sf9 cells (30×107 cells in a 275-cm2 flask) were infected with recombinant baculoviruses at a multiplicity of 10 and cultured at 27 C. for 48 hours. Expression was detected as follows.

The cells were washed in ice-cold phosphate-buffered saline, scraped into ice-cold lysis buffer (25 mM Tris, pH 7.5, 2 mM EDTA, 1 mM dithiothreitol, 0.1 mM benzamididine, 0.1 mM phenylmethylsulfonyl fluoride), and disrupted by sonication, and the resultant suspension was centrifuged at 2000×g for 10 minutes at 4 C. The supernatant was centrifuged at 100,000×g for 1 hour at 4 C. The supernatant from this second centrifugation was removed to give the cytosolic fraction and the pellet resuspended in lysis buffer. The resuspended pellet was centrifuged at 2000×g for 5 minutes. The supernatant obtained constituted the membrane fraction.

Twenty microliter samples of supernatant were collected and subjected to a 7.5% SDS-PAGE with a Laemmli buffer system on a 7.5% gel and stained with Coomassie Blue. The presence of a prominent 120 kD band was revealed that was not present in mock-transfected controls, consistent with the molecular mass expected for an approximately 1074 amino acid protein. The identity of the 120 kD band was confirmed using a rabbit anti-hPLD1a antisera.

Human PLD1a was also expressed in COS-7 cells. A fragment of the hPLD1a cDNA encoding the entire open reading frame (nucleotides 93 through 3603 of the cDNA) was subcloned in-frame downstream of the cytomegalovirus promoter and the Flu epitope tag in the mammalian expression vector pCGN. COS-7 cells were transfected with 3 g of the resulting plasmid, pFlu-hPLD1, using lipofectamine (Life Technologies, Inc.). Forty-eight hours later, the cells were assayed for PLD activity in the standard headgroup assay referenced below. The time course of choline release varied linearly over time and in proportion to the amount of protein added.

To confirm that hPLD1a encodes a PLD activity, cation-exchange HPLC was used to analyze the water-soluble product(s) that co-eluted with a labeled choline standard and thin layer chromatography was used to demonstrate concurrent production of PA. Both membrane-associated and cytosolic PLD activities have been described in mammalian tissues and cell lines and it ha been suggested that the membrane-associated and cytosolic PLD activities have distinct biochemical properties and might derive from different gene products. Samples of the reaction products were applied to a 1 ml HPLC column of Source 15S resin (Pharmacia Biotech Inc.) and washed with 10 ml of $H_2O$ and eluted with a 30 ml linear gradient of 0–1 M $CH_3COONH_4$ in water at a flow rate of 1 ml/min. 1 ml fractions were collected and their radioactivity determined by liquid scintillation counting. Compounds were identified by reference to authentic standards. For analysis of phospholipid products, the vescicles were of standard composition except that approximately 10–20×103 dpm of [$^{32}$P]PC, [$^{32}$P]PE or [$^{32}$P]PI (specific radioactivity 10,000 dpm/nmol) was substituted for the [$^3$H]PC. Incubations were exactly as described except that transphosphatidylation assay contained 2% v/v EtOH. The assays were terminated by addition of 232 1 of 1:1 $CHCl_2$, MeOH. After mixing and centrifugation, the lower phases were removed, dried under vacuum, and analyzed by TLC on oxalate-impregnated Whatman 60A silica gel plates in a solvent system of $CHCl_2$, MeOH:acetic acid (13:3:1, v/v). Products were visualized by autoradiography and identified by their mobilities relative to authentic standards. A band at 120 kD was observed in the hPLD1 lane and not observed in Sf9 cells infected with native baculovirus vector or PLC-expressing baculovirus vector. The identity of the 120 kD band was confirmed using rabbit anti-hPLD1 antisera.

Because of the possibility that other factors in cell extracts could affect enzymatic activity, the protein was purified to homogeneity to investigate its activities in isolation. An immunoaffinity procedure using immobilized affinity-purified anti-peptide antibodies was developed for this purpose, as follows.

a. Preparation of Affinity-purified Anti-PLD1 Peptide Antibodies

Two rabbits were immunized with a mixture of peptides corresponding to amino acid residues 1–15 and 525–541 of the sequence of hPLD1 and affinity-purified antibodies (termed Ab1 and Ab525 respectively) were isolated using standard procedures. These antibodies recognize PLD1a and PLD1b by western blotting and can immunoprecipitate their antigens under denaturing and non-denaturing conditions. The peptide antigens were chosen to generate antibodies that can distinguish PLD1 from PLD2.

b. Preparation of Immunoaffinity Resin 1 mg of a mixture of the two affinity-purified antibodies was adsorbed to 0.5 ml of protein-A coupled to Sepharose-$Cl^4B$ in phosphate buffered saline (PBS) for 1 hour at room temperature. The resin was washed with 0.2 M Na$^+$Borate, pH 9.0 and the antibodies covalently linked to the immobilized protein A by reaction with 20 mM dimethylpimelimidate in 0.2 M Na$^+$Borate, pH 9.0 for 30 minutes at room temperature with constant agitation. The reaction was quenched by washing the resin in 0.2 M ethanolamine, pH8, after which the resin was washed extensively and stored in PBS containing 0.1% $NaN_3$.

c. Expression

Recombinant baculoviruses for expression of PLD1b were generated, selected, purified and propagated using standard techniques. Monolayers of exponentially growing Sf9 cells (3×10 7 cells/225 cm$^2$ flask, two flasks for each purification) were infected with the viruses at a multiplicity of 10. The infected cells were grown for 48 hours, media removed and washed once with ice-cold phosphate-buffered saline. The cells were lysed on ice by addition of 5 ml/225 cm$^2$ flask of ice-cold lysis buffer containing 150 mM NaCl, 1% Nonidet P-40, 1 mM EGTA, 0.1 mM benzamidine, 0.1 mM PMSF, 10 g/ml pepstatin A, 10 g/ml leupeptin. After 30 minutes on ice, the cells were scraped up and the suspension centrifuged at 50,000×g for 30 minutes at 4 C. The supernatant obtained (10 mls) was mixed with 0.5 ml of the immunoaffinity resin and kept at 4 C. with constant agitation for 1 hour. The resin was sedimented by gentle centrifugation and unbound protein removed. The resin was washed three times with 25 volumes of lysis buffer. After the final wash, the resin was resuspended in 5 ml of lysis buffer and placed in a 10 ml BioRad disposable column. The resin was washed with 10 ml of 10 mM phosphate buffer, pH6.8 containing 1%-DOG as 3×0.5 ml fractions. The eluant was collected on ice into tubes containing 0.075 ml of 1 M phosphate buffer, pH8.0. ARF-stimulated PLD activity in these fractions was determined as described below and the fractions were also analyzed by SDS-PAGE and western blotting using standard procedures.

Expression of both PLD1a and PLD1b is considerably better when monolayers, as opposed to suspension cultures, of insect cells are used. In both cases however, large quantities of insoluble proteins accumulate. The active fraction of these recombinantly-expressed PLD enzymes is predominantly membrane-associated. The yield is approximately 10 g from two 225 cm$^2$ flasks. Identical purifications from Sf9 cells infected with a control baculovirus produced no detectable protein by SDS-PAGE, western blotting or activity measurement.

Although the most effective extraction of the proteins required detergent treatment, approximately 50% of the membrane-bound PLD activity could be extracted with 0.5 M NaCl. However, in the absence of detergents, enzyme activity was less stable. The purified proteins were kept at 4 C. in buffer containing 1%-DOG and were stable several days. PLD1 shows a pronounced tendency to aggregate during SDS-PAGE and this problem is exacerbated by boiling. Sample buffer containing 8 M urea at room temperature was therefore used to denature the proteins for SDS-PAGE.

The PLD sequence does not contain large stretches of hydrophobic residues indicative of regions involved in mambrane insertion. Purified PLD1 binds to sucrose-loaded phospholipid vesicles of various compositions with high affinity (Kd<1 M). PLD1 does not contain pleckstrin homology domains or C2 domains, protein motifs known to be involved in protein phospholipid interactions.

EXAMPLE 3

Catalytic Properties and Activation Requirements of Human PLD1a and PLD1b

To determine the activity encoded by recombinant hPLD1a, control and hPLD1a-encoding baculovirus-infected Sf9 cells were assessed using a standard headgroup release assay that measures the amount of tritiated headgroup (e.g. [$^3$H]choline) liberated by hydrolysis of the labeled substrate [$^3$H]PC. The assay procedure measures release of the choline headgroup from the radiolabeled PC and is based on a protocol previously described in Brown, Cell 75:1137–44 (1993). Using standard separation techniques, cytosolic and membrane fractions were prepared from uninfected Sf9 cells or Sf9 cells infected for 48 hours with the hPLD1 expressing baculovirus vector. Sf9 cells infected with native baculovirus vector or PLC-expressing baculovirus vector yielded modest PLD activity levels similar to untransfected cells. In contrast, Sf9 cells infected with hPLD1a-encoding baculovirus exhibited substantial cytosolic (32 fold above control) and membrane-associated (15-fold above control) PLD activity.

To assess hPLD1a's substrate specificity, the standard PLD assay was carried out using [$^{32}$P]PE and [$^{32}$P]PI following the method as describe in Brown, *Cell* 75: 1137–44 (1993). The results revealed the hPLD1a is unable to hydrolyze PE or PI. All substances exhibiting PLD activities described to date also function as transphophatidylases in the presence of primary alcohols, catalyzing the transfer of the phosphatidyl group from an appropriate substrate to the alcohol and thus generating phosphatidyl alcohol. To determine whether hPLD1a was capable of transphosphatidylase activity, EtOH was added to the reaction mixture and the products analyzed by thin layer chromatography. The results demonstrated that hPLD1a catalyzes the formation of [$^{32}$P]phosphatidylethanol when presented with [$^{32}$P]PC. Since PC-specific PLD is the only enzyme capable of catalyzing this particular reaction, hPLD1a must be a PC-specific PLD.

EXAMPLE 4

To investigate the properties of the purified PLD1 proteins in detail, the following experiments were performed.

a. Purification of G-proteins

Human ARF1 was bacterially-expressed and purified as described in Randazzo, *Methods Enzymol.* 257: 128–35 (1995) with a final step of hydroxylapatite chromatography (BioRad BioGel HTP). Human RhoA, Rac1 and cdc42 were modified to contain the sequence MEEEEYMPME at the amino terminus, expressed in Sf9 cells using baculovirus vectors, and purified by affinity chromatography using an immobilized monoclonal antibody as described in Heyworth, *Mol. Biol. Cell* 4: 1217–23 (1993). The purified G-proteins were concentrated to 1–10 mg/ml using an Amicon pressure concentrator with a PM-10 membrane and stored in aliquots at −80 C. In some cases, the G-proteins were pre-activated by EDTA-stripping and loading with GTP S.

b. Purification of protein kinase C-

Human PKC—was expressed in Sf9 cells using a baculovirus vector provided by David Burns (Parke Davis Pharmaceuticals, Inc.) and purified following the published procedure of Kitano, *Methods Enzymol.* 124: 349–51 (1986) with minor modifications. The purified protein was concentrated to approximately 0.1 mg/ml using an Amicon pressure concentrator with a PM30 membrane and stored in aliquots at −80 C.

c. PLD Assay

The basic PLD assay was performed as described in Hammond, *J. Biol. Chem.* 270: 29640–43 (1995) using headgroup-labeled phosphatidyl-choline. Lipids were prepared and labeled. Labeled choline was obtained from American Radiolabelled Chemicals Inc. (Catalog No. ART 284) and extracted with chloroform and methanol 100 ml chloroform/100 ml methanol/90 ml water (100,000 dpm/assay; 1.6 ml). The mixture was vortexed, spun and the bottom layer collected and added to the lipid mixture to give a final concentration of 67 mM PE (Avanti Polar Lipids, Alabaster, Ala., catalog no 850757), 7.6 mM PIP$_2$ (suspended in 20 mM Hepes, pH 7) and 5.4 mM PC (Avanti catalog no 850457). The labeled choline/lipid mixture was sonicated and vortexed until the lipids are dissolved. Sf9 cells were plated onto large flasks (30×106 cells/flask) and left to adhere. Once adhered, medium was removed and the cells were infected with virus (at 1:5 or 1:10) for 1 hour with gentle rocking. After that time, virus was removed and fresh medium added, and the cells left to grow for 48 hours at 27 C. Medium was removed from the flask and the cells were washed once with PBS and then lysed in 5 ml lysis buffer (25 mM Tris, 5 mM EDTA, pH 7.5). Cells were scraped out of the flask, placed on ice, sonicated for 10 seconds and centrifuged in a [type of machine] centrifuge for 10 minutes at 700 rpm. Supernatant was removed and spun at 30,000 rpm for 60 minutes. Supernatant from this second centrifugation was then removed, and the pellet was resuspended in 0.5 ml lysis buffer, votexed and allowed to settle out.

For the assay, the resulting supernatant containing PLD1 enzyme (1–10 ml) was combined with G-protein(s), 20 ml assay buffer (30 mM Na-Hepes, pH 7.5, 3 mM EGTA, 80 mM KCl, 1 mM DTT, 3.0 mM MgCl$_2$ and 2.0 mM CaCl$_2$) and 10 mM Hepes to make a total volume of 50 ml. 50 ml of the labeled lipid mixture was added, vortexed thoroughly, and incubated at 37 C. for 30 minutes. The reaction was stopped by adding 200 ml of 10% TCA and 100 ml of 10 mg/ml BSA and centrifugation for 5 minutes at 10,000 rpm. 350 ml of the supernatant was removed and counted in 2 ml of scintillation fluid using a LKB scintillation counter for 60 seconds. This was the basic assay used for the following experiments; any modifications were as described below.

To investigate the dependence of enzyme activity on calcium and magnesium, the concentrations of calcium and magnesium ions of the assay medium were varied. For some assays the lipid component of the vesicles was altered. Ptdins (4,5)P$_2$ was purified from a lipid extract of bovine brain as described in Hammond, supra. Synthetic Ptdins (3,4,5)P$_3$ was obtained from Glenn Prestwich, Dept. of Chemistry, SUNY Stony Brook. [$^{32}$P]-labeled phospholipids were isolated from extracts of U937 cells labeled overnight with [$^{32}$P] PO$_4$ 2- as described in Hammond, supra.

d. Regulation by Polyphosphoinositides

Vesicles containing 7% acidic lipid in a background of PE/PS were employed in the foregoing assay. The lipids tested were PI(4,5)P$_2$, PI(3,4,5)P$_3$, PI4P and PI. Only PI(4,5)P$_2$ and PI(3,4,5)P$_3$ stimulated the activity of PLD1. Maximal activation was observed with approximately 7% PI(4,5)P$_2$ or PI(3,4,5)P$_3$, although PI(4,5)P$_2$ was a more effective activator. At concentrations of up to 100 M, soluble inositol 1,4,5 trisphosphate neither activated PLD1 nor blocked activation by PI(4,5)P$_2$ or PI(3,4,5)P$_3$.

The stimulation effect for the lipids PI(4,5)P$_2$ and PI(3,4,5)P$_3$ is highly selective since a variety of other acidic phospholipids and phosphoinositides with different positional phosphate group substitutions were ineffective. It is possible that the presence of a low molar fraction of PI(4,5)P$_2$ alters the substrate-containing phospholipid surface in a manner that renders the PC substrate more readily hydrolyzed by the enzyme. Not all PLD activities are stimulated by PI(4,5)P$_2$ and the high degree of phospholipid headgroup selectivity coupled with the observation that PI(4,5)P$_2$ and PI(3,4,5)P$_3$ activate pure PLD1 suggests that activation involves a direct interaction between PLD1 and PI(4,5)P$_2$. Inspection of the primary sequence of PLD1 does not reveal homologies to other proteins known to interact with inositol lipids and phosphates. Phosphatidylinositol-specific phospholipase C-1 is activated by PI(4,5)P$_2$, which binds to an NH2-terminal non-catalytic site (a pleckstrin homology domain) anchoring the enzymes to the membrane allowing them to function in a scooting mode of catalysis. For this reason, binding of phosphatidylinositol-specific phospholipase C-1 to phospholipid vesicles and expression of processive catalytic activity are both markedly enhanced by inclusion of PIP$_2$ in the vesicle surface and inhibited by soluble Ins(1,4,5)P$_3$ which also binds to the NH$_2$-terminal PH-domain. These preliminary studies suggest that an analogous mechanism does not underlie the activation of PLD1 by PI(4,5)P$_2$; that is, Ins(1,4,5)P$_3$ neither activates PLD1 nor inhibits activation by PI(4,5)P$_2$. PI(4,5)P$_2$ does not alter the binding of PLD1 to sucrose-loaded phospholipid vesicles. Another possibility is that binding of PI(4,5)P$_2$ increases enzyme activity by some allosteric mechanism. In support of a direct interaction between PLD1 and PI(4,5)P$_2$, raedioloabeled photoreactive benzophenone-derivatives of PI(4,5)P$_2$ and PI(3,4,5)P$_3$ can balel crude and puriried preparations of PLD1. Since PI(4,5)P$_2$ and PI(3,4,5)P$_3$ are approximately equipotent activators of PLD1 in vitro, given the relative abundance of these two lipids in mammalian cells, PI(4,5)P$_2$ is the most likely candidate for a physiologic PLD activator.

e. Dependence on Ca$^{2+}$ and Mg$^{2+}$

ARF-stimulated PLD1activity was determined as the free concentrations of these ions were varied in the assay medium. PLD1 activity was insensitive to changes in Ca$^{2+}$ concentration over a side range (<10$^{-8}$ M to 10$^{-2}$ M). By contrast, ARF-stimulated PLD1 activity was dependent on Mg$^{2+}$ with half-maximal activity observed at approximately 10$^{-4}$ M.

f. Activation by ARF and Rho Family G-proteins

PLD1 was incubated with increasing concentrations of purified GTP S-activated ARF1(ADP-ribosylation factor 1), RhoA, Rac1 and cdc42. Half-maximal activation was observed with approximately 0.2 M ARF1. The three Rho family G-proteins were somewhat less potent activators of PLD1 with half-maximal effects observed at 1 M. ARF1 was the most effective activator producing an approximately 50-fold stimulation of the enzyme. RhoA and Rac1 stimulated the enzyme approximately 10- and 13-fold respectively and cdc42 produced an approximately 5-fold activation. Effects of ARF and Rac1 were clearly saturable and, although the concentrations of purified RhoA and cdc42 obtained limited the final concentrations achieved in the assay, at the highest concentrations used, effects of these activators also appeared to be approaching saturation. Activation of PLD1 by these G-proteins was strictly dependent on GTP S.

g. Activation by protein kinase C-

Purified PKC- stimulated PLD1 in a concentration dependent and saturable manner. Half-maximal effects of PKC- were observed with approximately 10 nM protein and the maximal effect of this activator (25-fold stimulation) was approximately 50% that observed with a maximally-effective concentration of ARF1. Inclusion of 100 mM phorbolmyristate acetate (PMA) in the assay medium increased the potency with which PKC- stimulated PLD1 by approximately 10-fold and the maximal effect by approximately 1.5-fold. PKC- Activation by PKC- was ATP-independent irrespective of the inclusion of PMA in the medium. When 0.1 mM ATP was included in the assays, PKC-stimulated PLD activity was somewhat lower than observed in the absence of ATP and the effect of PKC on PLD activity appeared to be more strongly dependent on PMA. Activation of PLD1 by ARF was unaffected by the inclusion of ATP. The PKC- used in the assays exhibited phosphatidylserine and diglyceride (or PMA) stimulated autophosphorylation and phosphorylation of histone under the same assay conditions.

h. Synergistic Effects of G-proteins and PKC- on PLD Activity

The ARF and Rho family G-proteins and PKC- activate PLD1 independently. Interactions between these regulators as activators of purified PLD1 was tested in the standard PLD assay.

Maximally effective concentrations of ARF1 (4.7 M), RhoA (3.8 M), Rac1 (5.3 M), cdc42 (5.5 M) and PMA-activated PKC- (0.043 M) produced 49-, 13-, 13-, 10- and 28-fold activations of PLD1 respectively. When this experiment was repeated including 4.7 M GTP S-activated ARF1 in each set of assays, the response to additional ARF1 was unchanged as expected by substantial increases in response to the Rho proteins were observed. In the presence of ARF1, activation by PKC- was increased to a 145-fold stimulation over basal activity. Similarly, responses to Rac1 and cdc42 were both increased to 106-fold of basal. Combination of PKC- with the Rho family G-proteins also produced a substantial activation of PLD1. When combined with RhoA, Rac1 or cdc42, PKC-stimulated PLD1 activity was increased 64-, 66- and 67-fold of basal respectively while ARF1 increased the response to PKC- to a 145-fold stimulation. By contrast, combinations of the three Rho proteins did not result in greater PLD1 activity than observed with each of the proteins alone. For example, RhoA alone produced a 13-fold activation of PLD1a nd PLD activity was not further increased by addition of concentrations of Rac1 or cdc42 that were sufficient to cause a maximal activation of PLD when added alone. Similar observations were made for combinations of Rac1 and cdc42. Combinations of maximally-effective concentrations of ARF1 and PKC- with each of the Rho family G-proteins produced a dramatic increase in PLD1 activity. As discussed above, combination of ARF1 and PKC- stimulate PLD1 activity to a level 145-fold over basal. In the presence of RhoA, Rac1 and cdc42, this was increased to 280-, 265- and 254-fold of basal activity.

The simplest explanation for these findings is that the PLD1 protein contains separate sites for interaction with PI(4,5)P$_2$, PI(3,4,5)P$_3$, ARF, the Pho family G-proteins and protein kinase C- and that occupancy of these sites by their respective ligands results in a co-operative increase in catalytic efficiency of the enzyme. Comparison of the primary sequences of plant, yeast and human PLD enzymes identifies four regions of homology including two regions containing sequences conserved among a family of related proteins that catalyze phospholipid synthesis reactions. It has been suggested that these sequences are important in catalysis, so it appears reasonable to postulate that other regions of the protein are involved in regulatory interactions with the lipid and protein factors.

i. PLD1 Functions

PLD1 may be uniquely positioned to receive and integrate different kinds of extracellular signals, transducing them to generate lipid-derived molecules that, in turn, mediate cell-specific responses. Given the growing evidence for involvement of ARF-activated PLD in intracellular protein trafficking, receptor-regulated secretion would be a good candidate for a PLD-1 mediated response. Another, not inconsistent, possibility is that PLD1 is present in different membrane compartments of the cell where different modes of regulation predominate and different downstream effectors are present. For example, ARF-dependent activation of PLD1 in the Golgi apparatus might generate PA for coated vesicle formation while PKC and/or Rho-dependent PLD activation of PLD1 in the plasma membrane could result in changes in cell morphology mediated by the actin cytoskeleton or lead to formation of diglyceride for PKC activation.

EXAMPLE 5

Comparison of hPLD1a and hPLD1b Functional Properties

To compare activation requirements of hPLD1a and hPLD1b, both enzymes were incubated with various combinations of activators in the presence of labeled PC and activity determined by measuring the amount of headgroup released in the standard headgroup release assay according to the methods of Brown, *Cell* 75, supra. The activation requirements of both enzymes were compared in each of the assays in Example 4 above. No differences in activation requirements between the hPLD1a and hPLD1b were found.

To analyze changes in the levels of hPLD1 a and hPLD1b during HL-60 cell differentiation induced by dcbAMP, HL-60 cells maintained in RPMI-1640 medium supplemented with 10% fetal bovine serum, 100 units/ml penicillin and 100 g/ml streptomycin in a humidified atmosphere containing 5% $CO_2$, at 37 C. were grown in RPMI-1640 medium without fetal bovine serum for 24 hours. Differentiation was initiated by the addition of 0.5 mM dbcAMP. Levels of PLD1a and PLD1b were quantified by RT-PCR. Total RNA was isolated from the HL-60 cells at the exponential growth stage by the acid guanidine thiocyanate method following the protocol of Chomczynski, *Anal. Biochem.* 162: 156–62(1992). Two g of RNA was reverse transcribed by using random hexamer mixed primers. The number of amplification cycles were determined to individual primer sets in order to maintain exponential rate of product amplification. Amplified DNA fragments were subjected to electrophoresis on 1.5% agarose gel and visualized by ethidium bromide staining. The intensity of bands was quantified by a densitometer (Atto Densitograph, Tokyo, Japan). Primer A (Forward): nucleotides 1475 through 1491; primer B (reverse) nucleotides 2133 through 2113 of SEQ ID NO: 1. Amplification conditions used were 94 C. for 30 seconds, 60 C. for 1 minute, and 72 C. for 1 minute; 25–27 cycles.

A 3–4 fold increase in hPLD1 was observed over the 3 day differentiation period. Both hPLD1a and hPLD1b increased, although PLD1a increased more rapidly. On day 1, hPLD1a exhibited an approximately 3-fold increase in activity and hPLD1b exhibited a slightly less than 2-fold increase in activity. On day 2, hPLD1a exhibited an approximately 4-fold increase in activity and hPLD1b exhibited an approximately 3-fold increase in activity. On day 3, hPLD1a exhibited a slightly lowered increased activity, slightly less than 4-fold, and hPLD1 b exhibited an approximately 3.5-fold increase in activity.

Since the magnitude of rise of hPLD1 is comparable to the increase over time of PtdBut, the increased levels of PLD1 activity can be most simply attributed to the increased levels of hPLD1 mRNA. This is analogous to the regulation of PLD in yeast, where levels of both activity and RNA are increased during meiosis when PLD activity is required in order for the process of sporulation to be completed. See, Rose, *Proc. Natl. Acad. Sci.* 92:12151–55 (1995).

EXAMPLE 6
Identification and Isolation of mPLD2, Another Member of the PLD Family of Enzymes mPLD2 was isolated using the coding sequence of hPLD1 as a probe under conditions of reduced stringency as described in Maniatis, *Molecular Cloning (A Laboratory Manual)*, Cold Spring Harbor Laboratory (1982) to identify related cDNAs. A 10.5 day embryonic mouse embryo cDNA library and a neonatal mouse brain cDNA library (both from Stratagene, La Jolla, Calif.) were screened and approximately twenty hybridizing cDNAs were identified. Once aligned, the cDNAs represented overlapping fragments of two unique sequences that encoded unique proteins related to hPLD1. One sequence, denoted mPLD1, encoded a protein having sequence identity of approximately 96% with hPLD1. The other sequence, denoted mPLD2, encoded a protein having sequence identity of approximately 50% with hPLD1. Approximately 10% of the mPLD2 amino terminal sequence was obtained using the RACE technique. Expressed sequence tags encoding a human protein having sequence identity of approximately 95% with mPLD2 were later identified in GenBank. These expressed sequence tags represent approximately 40% of the hPLD2 amino acid sequence.

mPLD2 activity was assessed as described in Example 3 for hPLD1. The mPLD2 protein coding sequence was subcloned in pCGN, an expression vector containing a CMV promoter, flu-epitope tag and an SV40 polyadenylation signal sequence. See Example 3. This plasmid was transfected into COS-7 cells and cell extracts assayed for PLD activity employing the standard headgroup assay of Example 3. mPLD2 was detected in quantities far above COS-7 background levels. The protein coding sequence of mPLD2 was also subcloned in a baculovirus vector following the protocol of Example 3. mPLD2 activity was successfully detected using the procedures described in Example 3.

EXAMPLE 8
RNA Regulation of hPLD2

From the data of Example 7, it was known that a human analog of mPLD2 existed. mPLD2 primers were made from the expressed sequence tags existing in GenBank. To analyze changes in the levels of hPLD2 activity during HL-60 cell differentiation induced by dcbAMP, HL-60 cells maintained in RPMI-1640 medium supplemented with 10% fetal bovine serum, 100 units.ml penicillin and 100 g/ml streptomycin in a humidified atmosphere containing 5% $CO_2$, at 37 C. were grown in RPMI-1640 medium without fetal bovine serum for 24 hours. Differentiation was initiated by the addition of 0.5 mM dbcAMP. Levels of hPLD2 were quantified later by RT-PCR. Total RNA was isolated from the HL-60 cells at the exponential growth stage by the acid guanidine thiocyanate method following the protocol of Chomczynski, *Anal. Biochem.* 162:156–62(1992). Two g of RNA was reverse transcribed by using random hexamer mixed primers. The number of amplification cycles were determined to individual primer sets in order to maintain exponential rate of product amplification. Amplified DNA fragments were subjected to electrophoresis on 1.5% agarose gel and visualized by ethidium bromide staining. The intensity of bands was quantified by a densitometer (Atto Densitograph, Tokyo, Japan). Primer E (Forward):

5'TCCTCCAGGCCATTCTGCACT 3'. Primer F (reverse):

5'CGTTGCTCTCAGCCATGTCTTG 3'. Amplification conditions used were 94 C. for 30 seconds, 60 C. for 1 minute, and 72 C. for 1 minute; 25–27 cycles.

PLD2 levels rose dramatically over the three day differentiation period to a level approximately 20-fold higher than in undifferentiated HL-60 cells. On day 1, hPLD2 exhibited an approximately 8-fold increase in activity. On day 2, hPLD2 exhibited an approximately 12-fold increase in activity. On day 3, hPLD2 exhibited an approximately 20-fold increase in activity.

Since total PLD activity levels did not rise as significantly, either PLD2 activation was not fully provoked by the fMLP and PMA stimuli, or the absolute amount of PLD2 is relatively small compared to PLD1.

EXAMPLE 9
Isolation and Cloning of hPLD2 hPLD2 is isolated using the coding sequence of mPLD2 as a probe under conditions of reduced stringency as described in Maniatis, *Molecular Cloning (A Laboratory Manual)*, Cold Spring Harbor Laboratory (1982) to identify related cDNAs. A human cDNA library is screened and hybridizing cDNAs are identified. hPLD2 activity is assessed as described in Example 3 for hPLD1. The hPLD2 protein coding sequence is subcloned in pCGN, an expression vector containing a CMV promoter, flu-epitope tag and an SV40 polyadenylation signal sequence. See Example 3. This plasmid is transfected into COS-7 cells and cell extracts assayed for PLD activity employing the standard headgroup assay of Example 3. The protein coding sequence of hPLD2 can also be subcloned in a baculovirus vector following the protocol of Example 3.

EXAMPLE 10

Discussion of Results of PLD1 and PLD2 Comparisons

PLD activation has been associated with two biological processes in vivo. First, PLD is now thought to play a role in accelerating ARF-mediated bud formation in the ER and Golgi, which is required for secretion. Second, PA, the biologically significant product of PC hydrolysis by PLD, has been shown to promote filamentous actin polymerization and stress fiber formation. A growing body of evidence suggests that there two processes are linked such that external signals lead to increased secretion in a polarized orientation relative to the inducing signal. These events require the participation of ARF, Rho, Rac and cdc42, all of which are activators of PLD1. Finally, differentiation of HL-60 cells into neutrophils is marked by increases in secretion of chemokines, and such secretion can be blocked by the inhibition of PLD activity. Taken together, these findings suggest that the up regulation of PLD1 may be required in order for HL-60 cells to increase their capability as neutrophils to release chemokines in a targeted manner upon exogenous stimulation by other immune cells.

The role of PLD2 in this process is currently unknown. More work is required to determine whether the increase in PLD1 and PLD2 is required for differentiated neutrophils to manifest their well characterized phenotypic behavior. These results also raise the question of whether PLD mRNA undergoes down regulation, for example after prolonged stimulation, which is marked by a loss in recruitable PLD activation.

The following bacterial strains containing the DNA sequences of the invention were deposited with the American Type Culture Collection (ATCC), 12301 Parklawn Drive, Rockville, Md., USA under the terms of the Budapest Treaty on the International Recognition of the Deposit of Microorganisms for purposes of patent Procedure and the Regulations thereunder. This assures maintenance of a viable culture for 30 years for the date of deposit. The organisms will be made available by the ATCC under the terms of the Budapest Treaty, and subject to an agreement between applicant ant the ATCC that assures unrestricted availability upon issuance of the pertinent U.S. patent. Availability of the deposited strains is not to be construed as a license to practice the invention in contravention of the rights granted under the authority of any government in accordance with its patent laws.

| Deposit Designation | ATCC No. | Deposit Date |
| --- | --- | --- |
| Plasmid phPLD1a | 97693 | 08/26/96 |
| Plasmid phPLD1b | 97694 | 08/26/96 |
| Plasmid phPLD2 | 97695 | 08/26/96 |

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. An isolated polypeptide comprising an amino acid sequence selected form the group consisting of SEQ ID No. 2, SEQ ID No. 4, and SEQ ID No. 6.

2. A polypeptide encoded by a DNA sequence selected from the Group consisting of SEQ ID No. 1, SEQ ID No. 3, and SEQ ID No. 5.

3. An isolated polypeptide comprising SEQ ID No. 2.

4. An isolated polypeptide comprising SEQ ID No. 4.

5. An isolated polypeptide comprising SEQ ID No. 6.

6. A polypeptide encoded by a DNA sequence comprising SEQ ID No. 1.

7. A polypeptide encoded by a DNA sequence comprising SEQ ID No. 3.

8. A polypeptide encoded by a DNA sequence comprising SEQ ID No. 5.

9. A polypeptide encoded by a nucleotide sequence that hybridizes under stringent conditions to a nucleotide sequence selected from the Group consisting of SEQ ID No. 1, SEQ ID No. 3, and SEQ ID No. 5.

10. An isolated polypeptide of claims 1, 2, or 9 in combination with a G-protein.

11. A composition of claim 10 wherein said G-protein is selected from the group consisting of ADP-ribosylation factor 1, RhoA, Rac1 and Cdc42.

* * * * *